United States Patent
Frankowski et al.

(10) Patent No.: US 9,663,521 B2
(45) Date of Patent: May 30, 2017

(54) COMPOUNDS AND METHODS FOR THE PREVENTION AND TREATMENT OF TUMOR METASTASIS AND TUMORIGENESIS

(71) Applicants: THE UNITED STATES OF AMERICA, as represented by THE SECRETARY, DEPARTMENT OF HEALTH AND HUMAN SERVICES, Washington, DC (US); UNIVERSITY OF KANSAS, Lawrence, KS (US); NORTH-WESTERN UNIVERSITY, Evanston, IL (US)

(72) Inventors: Kevin Frankowski, Lawrence, KS (US); Samarjit Patnaik, Gaithersburg, MD (US); Sui Huang, Chicago, IL (US); Juan Jose Marugan, Gaithersburg, MD (US); John Norton, San Diego, CA (US); Frank J. Schoenen, Lawrence, KS (US); Noel Terrence Southall, Potomac, MD (US); Steven Titus, Elkridge, MD (US); Wei Zheng, Potomac, MD (US)

(73) Assignees: The United States of America, as represented by the Secretary, Department of Health and Human Services, Washington, DC (US); University of Kansas, Lawrence, KS (US); Northwestern University, Evanston, IL (US)

( * ) Notice: Subject to any disclaimer, the term of this patent is extended or adjusted under 35 U.S.C. 154(b) by 0 days.

(21) Appl. No.: 14/364,759

(22) PCT Filed: Dec. 17, 2012

(86) PCT No.: PCT/US2012/070155
§ 371 (c)(1),
(2) Date: Jun. 12, 2014

(87) PCT Pub. No.: WO2013/090912
PCT Pub. Date: Jun. 20, 2013

(65) Prior Publication Data
US 2014/0323438 A1 Oct. 30, 2014

Related U.S. Application Data

(60) Provisional application No. 61/576,780, filed on Dec. 16, 2011.

(51) Int. Cl.
C07D 487/04 (2006.01)
A61K 31/519 (2006.01)
A61K 31/695 (2006.01)
A61K 45/06 (2006.01)
C07F 7/18 (2006.01)
A61P 35/02 (2006.01)
A61P 35/04 (2006.01)

(52) U.S. Cl.
CPC .......... C07D 487/04 (2013.01); A61K 31/519 (2013.01); A61K 31/695 (2013.01); A61K 45/06 (2013.01); C07F 7/1868 (2013.01)

(58) Field of Classification Search
CPC ............................ C07D 487/04; A61K 31/519
See application file for complete search history.

(56) References Cited

U.S. PATENT DOCUMENTS 6,455,534 B2 9/2002 Bridges et al.
2003/0036545 A1 2/2003 Castelhano et al.
(Continued)

FOREIGN PATENT DOCUMENTS

EP 0795556 A1 9/1997
JP 2011-507910 A 3/2011
(Continued)

OTHER PUBLICATIONS

STN printout, Interbioscreen Ltd., compound registry No. 510723-85-0, downloaded Sep. 3, 2015.*
STN printout, Ambinter, compound registry No. 573942-57-1, downloaded Sep. 3, 2015.*
Interbioscreen Ltd. (RN# 842969-23-7, Mar. 6, 2005).*
Abou El Ella et al. "Molecular modeling study and synthesis of novel pyrrolo[2,3d]pyrimidines and pyrrolotriazolopyrimidines of expected antitumor and radioprotective activities" Biorganic and Medicinal Chemistry 16: 2391-2402 (2008).
BasyoUni et al. "Pyrrolo[2,3-d]pyrimidines. Part 2. Synthesis of some new Pyrrolo[2,3-d]pyrimidin-4-amines and other related derivatives with molluscicidal properties" J. Chem. Research (S) p. 127 (1996).
(Continued)

Primary Examiner — Susanna Moore
(74) Attorney, Agent, or Firm — Leydig, Voit & Mayer, Ltd.

(57) ABSTRACT

The disclosure provides compounds for reducing the prevalence of the perinucleolar compartment in cells, for example, of formula (I), wherein $R^1$, $R^2$, $R^3$, and $R^4$ are as defined herein, that are useful in treating a disease or disorder associated with increased prevalence of the perinucleolar compartment, such as cancer. Also disclosed is a composition containing a pharmaceutically acceptable carrier and at least one compound embodying the principles of the invention, and a method of treating or preventing cancer in a mammal.

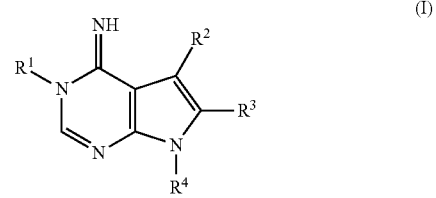

19 Claims, 1 Drawing Sheet

(56) References Cited

U.S. PATENT DOCUMENTS

| | | |
|---|---|---|
| 2003/0114467 A1 | 6/2003 | Shakespeare et al. |
| 2003/0187001 A1 | 10/2003 | Calderwood et al. |
| 2009/0163545 A1 | 6/2009 | Goldfarb |

FOREIGN PATENT DOCUMENTS

| | | |
|---|---|---|
| WO | WO 2009/042294 A2 | 4/2009 |
| WO | WO 2011/046646 A2 | 4/2011 |

OTHER PUBLICATIONS

El-Bayouki et al. "Synthesis of new pyrrole and pyrrolo[2,3-d]pyrimidine derivatives of potential antioxidant activity" Coll Czech. Chem. Commun. 75, No. 8: 813-834 (2010).

STN Registry Nos. 627053-75-2, 627053-71-8, 627053-69-4, 677791-41-4, 2003.

Office Action, Japanese Patent Application No. 2014-547550, mailed Jul. 19, 2016, 11 pages.

Ali, A.S. et al. "New Derivatives of pyrrolo[3,2-e][1,2,4] triazolo [1,5-c[pyrimidines" Egyptian Journal of Pharmaceutical Sciences 33: 473-484 (1992).

CAS Registry No. 831246-08-3, STN entry date: Feb. 15, 2005.
CAS Registry No. 791040-50-1, STN entry date: Dec. 1, 2004.
CAS Registry No. 785026-39-3, STN entry date: Nov. 21, 2004.
CAS Registry No. 769097-72-5, STN entry date: Oct. 25, 2004.
CAS Registry No. 763904-79-6, STN entry date: Oct. 15, 2004.
CAS Registry No. 730239-17-5, STN entry date: Aug. 22, 2004.
CAS Registry No. 727999-82-8, STN entry date: Aug. 18, 2004.
CAS Registry No. 627053-79-6, STN entry date: Dec. 15, 2003.
CAS Registry No. 627053-77-4, STN entry date: Dec. 15, 2003.
CAS Registry No. 627053-67-2, STN entry date: Dec. 15, 2003.
CAS Registry No. 627053-04-7, STN entry date: Dec. 15, 2003.
CAS Registry No. 578701-79-8, STN entry date: Sep. 4, 2003.

Office Action, Australian Patent Application No. 2012353651, dated Sep. 2, 2016, 10 pages.

Abou El Ella et al., "Molecular modeling study and synthesis of novel pyrrolo[2,3-d]pyrimidines and pyrrolotriazolopyrimidines of expected antitumor and radioprotective activities," *Bioorg. Med. Chem.*, 16 (5), 2391-2402 (2008).

El-Bayouki et al., "Synthesis of new pyrrole and pyrrolo[2,3-d] pyrimidine derivatives of potential antioxidant activity," *Collect. Czech. Chem. Commun.*, 75 (8), 813-834 (2010).

International Search Report, Application No. PCT/US2012/070155, dated May 2, 2013.

International Preliminary Report on Patentability, Application No. PCT/US2012/070155, dated Jun. 17, 2014.

Jin et al., "Identification of hNopp140 as a binding partner for doxorubicin with a phage display cloning method," *Chem. Biol.*, 9 (2), 157-162 (2002).

Kamath et al., "Perinucleolar compartment prevalence has an independent prognostic value for breast cancer," *Cancer Res.*, 65 (1), 246-253 (2005).

Norton et al., "Synthesis and anticancer activities of 6-amino amonafide derivatives," *Anticancer Drugs*, 19 (1), 23-36 (2008).

Norton et al., "The perinucleolar compartment is directly associated with DNA," *J. Biol. Chem.*, 284 (7), 4090-4101 (2009).

Pollock et al., "The Perinucleolar Compartment," *Cold Spring Harbor Perspectives in Biology*, 2 (2), 1-10 (2010).

Slusarczyk et al., Structure and function of the perinucleolar compartment in cancer cells, *Cold Spring Harb. Symp. Quant. Biol.*, 75, 599-605 (2010).

Written Opinion of the International Searching Authority, Application No. PCT/US2012/070155, dated Jun. 16, 2014.

\* cited by examiner

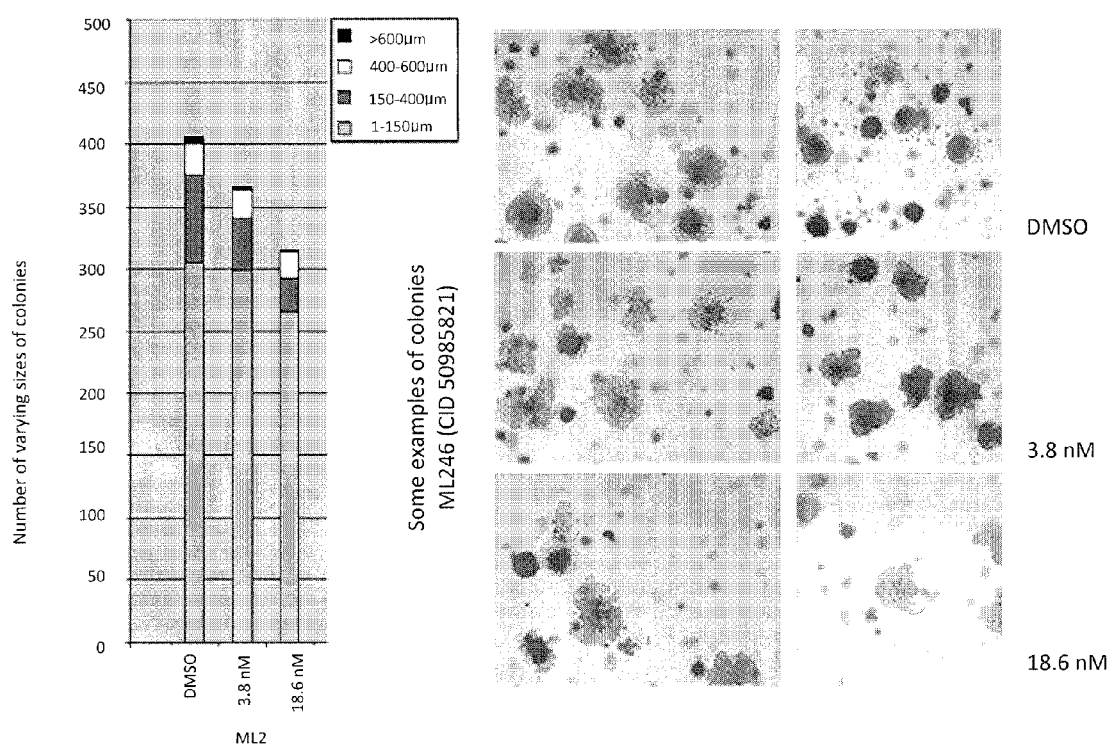

COMPOUNDS AND METHODS FOR THE PREVENTION AND TREATMENT OF TUMOR METASTASIS AND TUMORIGENESIS

CROSS-REFERENCE TO A RELATED APPLICATION

This patent application is the U.S. national phase of International Patent Application No. PCT/US2012/070155, filed Dec. 17, 2012, which claims the benefit of U.S. Provisional Patent Application No. 61/576,780, filed Dec. 16, 2011, which are incorporated by reference.

STATEMENT OF GOVERNMENT INTEREST

This invention was made with government support under R01 GM078555, R03MH082371 and U54 HG005031 awarded by the National Institutes of Health. The government has certain rights in the invention.

BACKGROUND OF THE INVENTION

Metastasis is the cellular mechanism used by disease to spread from an organ to another non-adjacent part of the organism. This process is particularly important in the development of solid tumors and is responsible for the majority of deaths associated with this disease. It is well recognized in the field that treatment of a tumoral lesion has a better prognosis if started in a pre-metastatic stage. In the last decade, although understanding of the underlying mechanisms involved in metastasis has advanced, the therapeutic tools impacting specifically the metastatic process are very limited.

SUMMARY

Inhibitors of the perinucleolar compartment (PNC), a subnuclear body characterized by its location to the periphery of the nucleolus and which is associated with malignancy both in vitro and in vivo, are disclosed as a solution to the unmet need for treating cancer, specifically the metastatic cancers. Compounds embodying aspects of the invention disrupt the assembly of the PNC. Such disruption reduces (without overt cytotoxicity) the prevalence in cells of a multicomponent subnuclear structure that is highly prevalent in metastatic tumors and for which presence (of the structure) positively correlates with metastatic capacity. In accordance with the invention, the present disclosure provides compositions comprising these compounds and methods of using these compounds as therapeutic agents in the treatment of cancer.

The disclosure provides a pharmaceutical composition comprising a compound or salt embodying the principles of the invention and a pharmaceutically acceptable carrier.

The disclosure further provides a method for treating or preventing cancer in a mammal, comprising administering to a mammal in need thereof a compound embodying the principles of the invention or a pharmaceutically acceptable salt thereof.

The disclosure additionally provides a method for disrupting a PNC in a cell, comprising contacting the cell with a compound embodying the principles of the invention or a pharmaceutically acceptable salt thereof.

The disclosure further provides a method for reducing the prevalence of perinucleolar compartment in a cell, comprising contacting the cell with a compound embodying the principles of the invention or a pharmaceutically acceptable salt thereof.

The disclosure further provides a method for reducing ATP levels produced by metastatic cancer cells, in a mammal afflicted with metastatic cancer, comprising administering to a mammal in need thereof a compound embodying the principles of the invention or a pharmaceutically acceptable salt the The disclosure additionally provides a method for reducing the colony formation of cancer cells in a mammal, comprising administering to a mammal in need thereof a compound embodying the principles of the invention or a pharmaceutically acceptable salt thereof.

The disclosure additionally provides a method for reducing the migration of cancer cells in a mammal, comprising administering to a mammal in need thereof a compound embodying the principles of the invention or a pharmaceutically acceptable salt thereof.

BRIEF DESCRIPTION OF THE SEVERAL VIEWS OF THE DRAWING

FIG. 1 illustrates a histogram representing the number and size of PC3M soft agar colonies after 14 days of treatment with a representative embodiment of the invention at two different concentrations, as well as representative images of colonies observed at these concentrations.

DETAILED DESCRIPTION OF THE INVENTION

In one embodiment, the invention provides a compound of the formula:

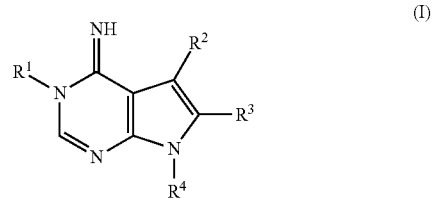

(I)

wherein $R^1$ is selected from alkyl, hydroxyalkyl, thioalkyl, alkoxyalkyl, alkylthioalkyl, cycloalkyl, hydroxycycloalkyl, hydroxycycloalkylalkyl, thiocycloalkyl, alkoxycycloalkyl, alkylthiocycloalkyl, dialkylaminoalkyl, heterocyclyl, heterocyclylalkyl, heteroaryl, arylalkyl, arylalkylpiperidin-4-yl, arylpiperazinylalkyl, and heteroarylalkyl, $R^2$ is aryl or heteroaryl, $R^3$ is selected from H, alkyl, cycloalkyl, aryl, heteroaryl, arylalkyl, and heteroarylalkyl, $R^4$ is selected from alkyl, cycloalkyl, cycloalkylalkyl, aryl, heteroaryl, arylalkyl, and heteroarylalkyl, or a pharmaceutically acceptable salt thereof, wherein $R^1$, $R^2$, $R^3$, and $R^4$, other than H, are optionally substituted on the aryl and/or alkyl portion with one or more substituents selected from halo, alkyl, hydroxyalkyl, thioalkyl, alkoxy, alkylthioalkyl, alkoxycarbonyl, alkylthiocarbonyl, amino, alkylamino, dialkylamino, aminosulfonyl, hydroxyl, perfluoroalkoxy, alkylenedioxy, and alkylcarbonyl, with the proviso that when $R^2$ and $R^3$ are both unsubstituted phenyl and $R^4$ is unsubstituted benzyl, $R^1$ is not 3-hydroxypropyl.

In accordance with an embodiment, $R^2$ is phenyl, optionally substituted with one or more substituents selected from halo, alkyl, hydroxyalkyl, thioalkyl, alkoxy, alkylthioalkyl, alkoxycarbonyl, alkylthiocarbonyl, amino, alkylamino, dialkylamino, and alkylcarbonyl.

In accordance with certain embodiments, $R^2$ is phenyl.

In accordance with any of the above embodiments, $R^3$ is phenyl, optionally substituted with one or more substituents selected from halo, alkyl, hydroxyalkyl, thioalkyl, alkoxy, alkylthioalkyl, alkoxycarbonyl, alkylthiocarbonyl, amino, alkylamino, dialkylamino, and alkylcarbonyl.

In accordance with any of the above embodiments, $R^4$ is benzyl, wherein the phenyl ring is optionally substituted with one or more substituents selected from alkyl, hydroxyalkyl, thioalkyl, alkoxy, alkylthioalkyl, alkoxycarbonyl, alkylthiocarbonyl, amino, alkylamino, dialkylamino, aminosulfonyl, hydroxyl, perfluoroalkoxy, and alkylcarbonyl.

In accordance with any of the above embodiments, $R^4$ is benzyl.

In accordance with any of the above embodiments, $R^1$ is a 5 or 6-membered heterocyclyl group having at least one hetero atom selected from O, N, and S; a hydroxy $C_1$-$C_7$ cycloalkyl group; a hydroxy $C_1$-$C_6$ alkyl group; a N,N-di($C_1$-$C_6$ alkyl)amino $C_1$-$C_6$ alkyl group; a $C_1$-$C_6$ alkoxy $C_1$-$C_6$ alkyl group; a heteroaryl $C_1$-$C_6$ alkyl group; a heterocyclyl $C_1$-$C_6$ alkyl group; phenyl $C_1$-$C_6$ alkyl group wherein the phenyl ring is substituted with one or more $C_1$-$C_6$ alkoxy groups; N-benzyl piperazinyl; N-phenyl piperazinylalkyl; a phenyl $C_1$-$C_6$ alkyl group where the alkyl is substituted with a hydroxy group; or a 5 or 6 membered heteroarylamino $C_1$-$C_6$ alkyl group wherein the heteroaryl group has at least one hetero atom selected from O, N, and S.

In accordance with certain preferred embodiments, $R^1$ is selected from the following:

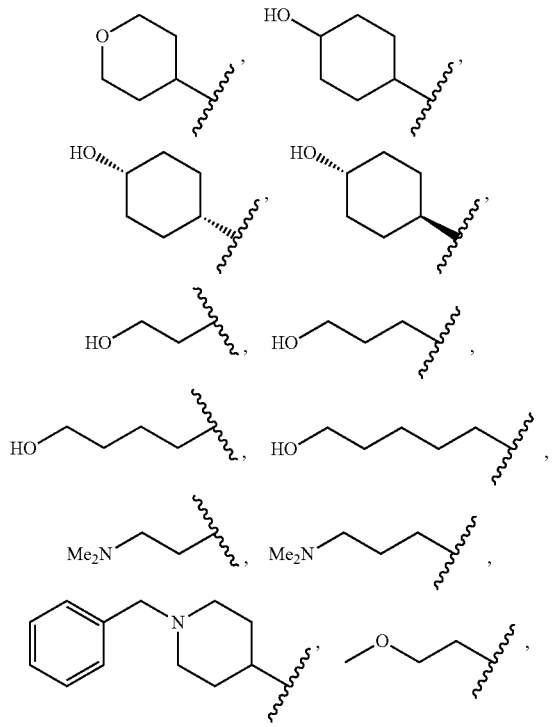

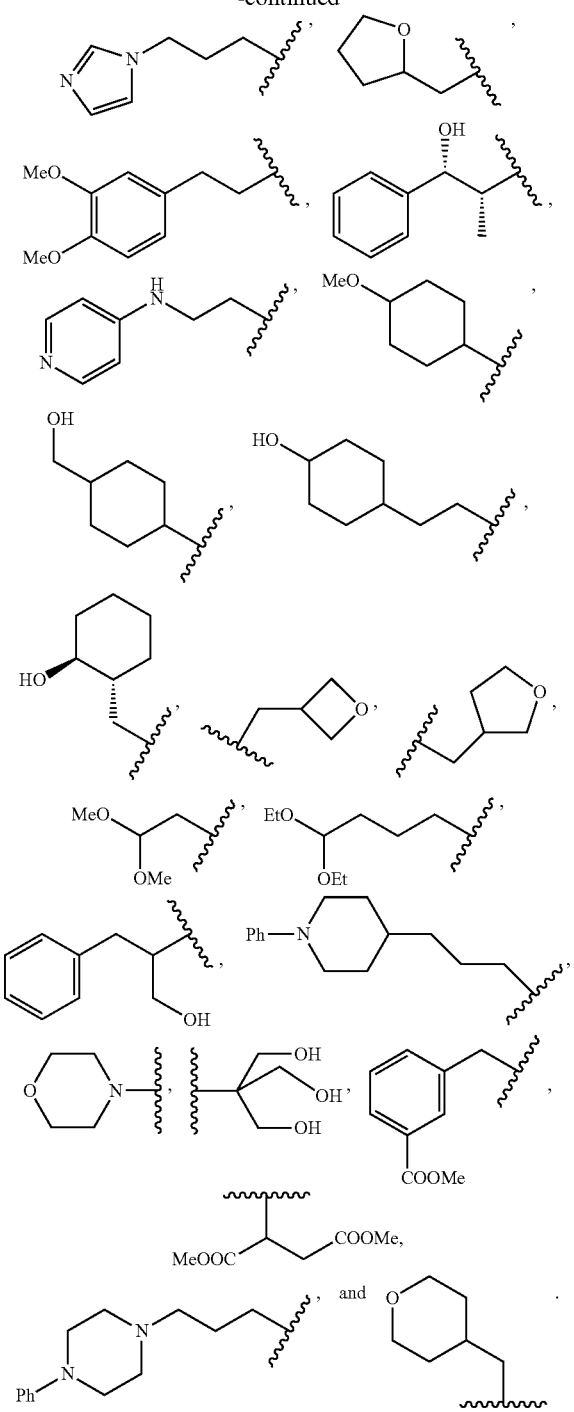

In accordance with certain specific embodiments, $R^2$ is phenyl, $R^3$ is phenyl, $R^4$ is benzyl, and $R^1$ is selected from the following:

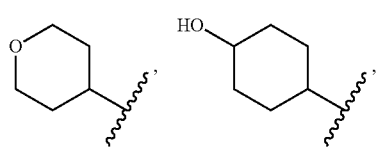

-continued

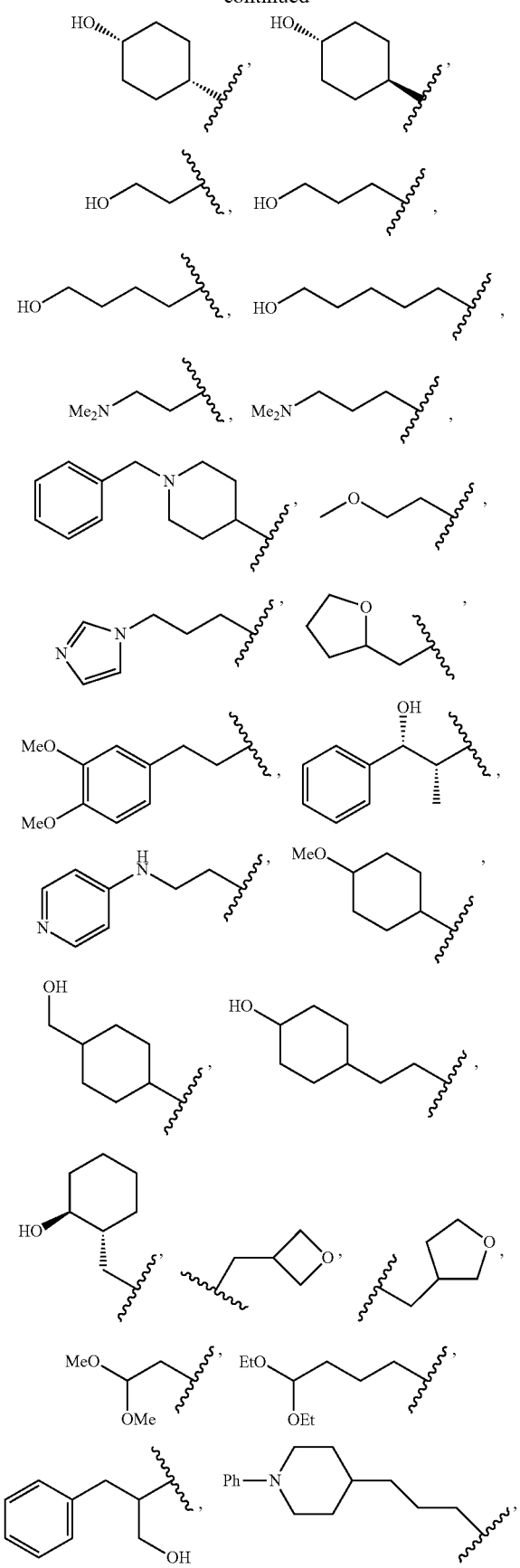

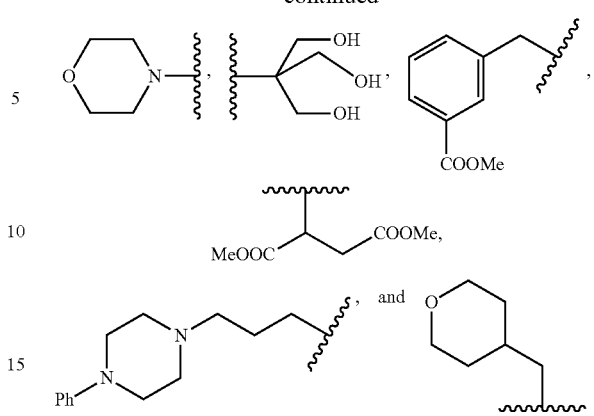

In accordance with certain embodiments, R⁴ is 4-methoxybenzyl.

In accordance with certain preferred embodiments, R¹ is selected from the following:

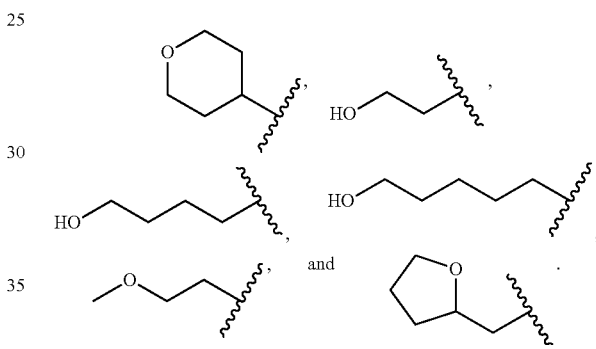

In accordance with certain specific embodiments, R² is phenyl, R³ is phenyl, R⁴ is 4-methoxybenzyl, and R¹ is selected from the following:

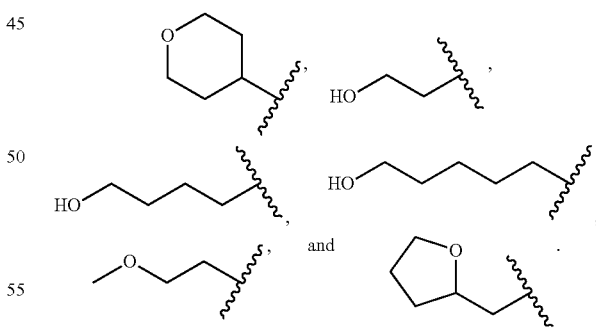

In accordance with any of the above embodiments, R⁴ is phenylethyl, wherein the phenyl ring is optionally substituted with one or more substituents selected from alkyl, hydroxyalkyl, alkoxy, and alkoxycarbonyl.

In accordance with certain embodiments, R⁴ is phenylethyl.

In accordance with certain preferred embodiments, R¹ is selected from the following:

In accordance with certain specific embodiments, $R^2$ is phenyl, $R^3$ is phenyl, $R^4$ is phenylethyl, and $R^1$ is selected from the following:

In accordance with certain embodiments, $R^4$ is heteroaryl $C_1$-$C_6$ alkyl.

In accordance with certain embodiments, $R^4$ is

In accordance with certain preferred embodiments, $R^1$ is selected from the following:

In accordance with certain specific embodiments, $R^2$ is phenyl, $R^3$ is phenyl, $R^4$ is and R[1] is selected from the following:

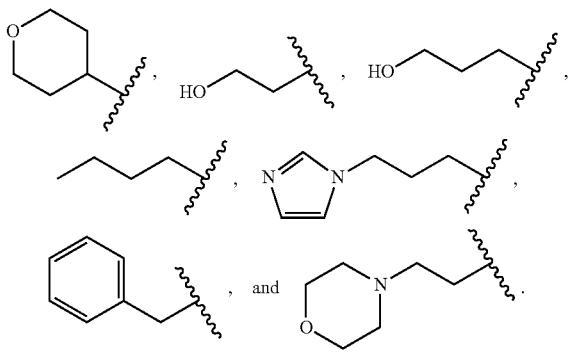

In accordance with certain embodiments, R[4] is selected from 4-aminosulfonylbenzyl, 4-trifluoromethoxybenzyl, 4-methoxybenzyl, and cyclopropylmethyl.

In accordance with certain preferred embodiments, R[1] is selected from the following:

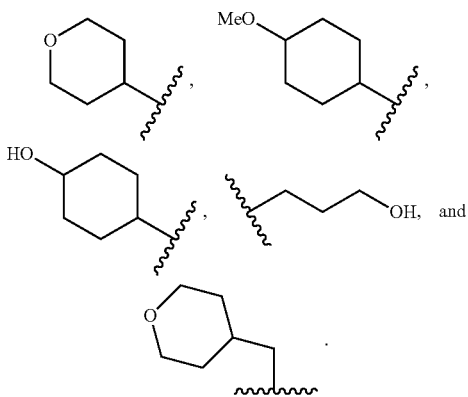

Referring now to terminology used generically herein, the teen "alkyl" means a straight-chain or branched alkyl substituent containing from, for example, 1 to about 6 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like.

The term "alkenyl," as used herein, means a linear alkenyl substituent containing at least one carbon-carbon double bond and from, for example, about 2 to about 6 carbon atoms (branched alkenyls are about 3 to about 6 carbons atoms), preferably from about 2 to about 5 carbon atoms (branched alkenyls are preferably from about 3 to about 5 carbon atoms), more preferably from about 3 to about 4 carbon atoms. Examples of such substituents include vinyl, propenyl, isopropenyl, n-butenyl, sec-butenyl, isobutenyl, tert-butenyl, pentenyl, isopentenyl, hexenyl, and the like.

The term "alkynyl," as used herein, means a linear alkynyl substituent containing at least one carbon-carbon triple bond and from, for example, 2 to about 6 carbon atoms (branched alkynyls are about 3 to about 6 carbons atoms), preferably from 2 to about 5 carbon atoms (branched alkynyls are preferably from about 3 to about 5 carbon atoms), more preferably from about 3 to about 4 carbon atoms. Examples of such substituents include ethynyl, propynyl, isopropynyl, n-butynyl, sec-butynyl, isobutynyl, tert-butynyl, pentynyl, isopentynyl, hexynyl, and the like.

The term "cycloalkyl," as used herein, means a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The cyclic alkyl groups may be unsubstituted or further substituted with alkyl groups such as methyl groups, ethyl groups, and the like. The term "cycloalkylalkyl," as used herein, refers to an alkyl group linked to a cycloalkyl group and further linked to a molecule via the alkyl group.

The term "heterocyclyl," as used herein, refers to a monocyclic or bicyclic 5- or 6-membered ring system containing one or more heteroatoms selected from the group consisting of O, N, S, and combinations thereof. The heterocyclyl group can be any suitable heterocyclyl group and can be an aliphatic heterocyclyl group, an aromatic heterocyclyl group, or a combination thereof. The heterocyclyl group can be a monocyclic heterocyclyl group or a bicyclic heterocyclyl group. Suitable bicyclic heterocyclyl groups include monocylic heterocyclyl rings fused to a $C_6$-$C_{10}$ aryl ring. When the heterocyclyl group is a bicyclic heterocyclyl group, both ring systems can be aliphatic or aromatic, or one ring system can be aromatic and the other ring system can be aliphatic as in, for example, dihydrobenzofuran. Non-limiting examples of suitable aromatic heterocyclyl groups include tetrahydrofuranyl, tetrahydropyranyl, tetrahydrothiopheneyl, pyrrolidinyl, piperidinyl, and morpholinyl. Non-limiting examples of suitable aromatic heterocyclyl groups include furanyl; thiopheneyl; pyrrolyl; pyrazolyl; imidazolyl; 1,2,3-triazolyl; 1,2,4-triazolyl; isoxazolyl; oxazolyl; isothiazolyl; thiazolyl; 1,3,4-oxadiazol-2-yl; 1,2,4-oxadiazol-2-yl; 5-methyl-1,3,4-oxadiazole; 3-methyl-1,2,4-oxadiazole; pyridinyl; pyrimidinyl; pyrazinyl; triazinyl; benzofuranyl; benzothiopheneyl; indolyl; quinolinyl; isoquinolinyl; benzimidazolyl; benzoxazolinyl; benzothiazolinyl; and quinazolinyl. The heterocyclyl group is optionally substituted with 1, 2, 3, 4, or 5 substituents as recited herein such as with alkyl groups such as methyl groups, ethyl groups, and the like, or with aryl groups such as phenyl groups, naphthyl groups and the like, wherein the aryl groups can be further substituted with, for example halo, dihaloalkyl, trihaloalkyl, nitro, hydroxy, alkoxy, aryloxy, amino, substituted amino, alkylcarbonyl, alkoxycarbonyl, arylcarbonyl, aryloxycarbonyl, thio, alkylthio, arylthio, and the like, wherein the optional substituent can be present at any open position on the heterocyclyl group.

The term "heterocyclylalkyl," as used herein, refers to an alkyl group linked to a heterocyclyl group and further linked to a molecule via the alkyl group.

The term "arylalkyl," as used herein, refers to an alkyl group linked to a $C_6$-$C_{10}$ aryl ring and further linked to a molecule via the alkyl group. The term "alkylaryl," as used herein, refers to a $C_6$-$C_{10}$ aryl ring linked to an alkyl group and further linked to a molecule via the aryl group.

The term "alkylcarbonyl," as used herein, refers to an alkyl group linked to a carbonyl group and further linked to a molecule via the carbonyl group, such as alkyl-C(=O)—. The term "alkoxycarbonyl," as used herein, refers to an alkoxy group linked to a carbonyl group and further linked to a molecule via the carbonyl group, such as alkyl-O—C(=O)—.

Whenever a range of the number of atoms in a structure is indicated (such as a $C_1$-$C_{12}$, $C_1$-$C_8$, $C_1$-$C_6$, $C_1$-$C_4$, or $C_2$-$C_{12}$, $C_2$-$C_8$, $C_2$-$C_6$, $C_2$-$C_4$ alkyl, alkenyl, alkynyl, etc.), it is specifically contemplated that any sub-range or individual number of carbon atoms falling within the indicated range also can be used. Thus, for instance, the recitation of a range of 1-8 carbon atoms (such as $C_1$-$C_8$), 1-6 carbon atoms (such as $C_1$-$C_6$), 1-4 carbon atoms (such as $C_1$-$C_4$), 1-3 carbon atoms (such as $C_1$-$C_3$), or 2-8 carbon atoms (such as $C_2$-$C_8$) as used with respect to any chemical group (such as alkyl, alkylamino, etc.) referenced herein encompasses and specifically describes 1, 2, 3, 4, 5, 6, 7, 8, 9, 10, 11, or 12 carbon atoms, and combinations thereof, as appropriate, as well as any sub-range thereof (such as 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate). Similarly, the recitation of a range of 6-10 carbon atoms (such as, $C_6$-$C_{10}$) as used with respect to any chemical group (such as, aryl) referenced herein encompasses and specifically describes 6, 7, 8, 9, and/or 10 carbon atoms, as appropriate, as well as any sub-range thereof (such as, 6-10 carbon atoms, 6-9 carbon atoms, 6-8 carbon atoms, 6-7 carbon atoms, 7-10 carbon atoms, 7-9 carbon atoms, 7-8 carbon atoms, 8-10 carbon atoms, and/or 8-9 carbon atoms, etc., as appropriate).

The term "halo" or "halogen," as used herein, means a substituent selected from Group VIIA, such as, for example, fluorine, bromine, chlorine, and iodine.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise 4n+2π electrons, according to Hückel's Rule.

The phrase "pharmaceutically acceptable salt" is intended to include non-toxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media such as ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p. 1445, and *Journal of Pharmaceutical Science*, 66, 2-19 (1977).

Suitable bases include inorganic bases such as alkali and alkaline earth metal bases, such as those containing metallic cations such as sodium, potassium, magnesium, calcium and the like. Non-limiting examples of suitable bases include sodium hydroxide, potassium hydroxide, sodium carbonate, and potassium carbonate. Suitable acids include inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, maleic acid, tartaric acid, fatty acids, long chain fatty acids, and the like. Preferred pharmaceutically acceptable salts of inventive compounds having an acidic moiety include sodium and potassium salts. Preferred pharmaceutically acceptable salts of inventive compounds having a basic moiety (such as a dimethylaminoalkyl group) include hydrochloride and hydrobromide salts. The compounds of the present invention containing an acidic or basic moiety are useful in the form of the free base or acid or in the form of a pharmaceutically acceptable salt thereof.

It should be recognized that the particular counterion forming a part of any salt of this invention is usually not of a critical nature, so long as the salt as a whole is pharmacologically acceptable and as long as the counterion does not contribute undesired qualities to the salt as a whole.

It is further understood that the above compounds and salts may form solvates, or exist in a substantially uncomplexed form, such as the anhydrous form. As used herein, the term "solvate" refers to a molecular complex wherein the solvent molecule, such as the crystallizing solvent, is incorporated into the crystal lattice. When the solvent incorporated in the solvate is water, the molecular complex is called a hydrate. Pharmaceutically acceptable solvates include hydrates, alcoholates such as methanolates and ethanolates, acetonitrilates and the like. These compounds can also exist in polymorphic forms.

In any of the above embodiments, the compound or salt of formula (I) can have at least one asymmetric carbon atom. When the compound or salt has at least one asymmetric carbon atom, the compound or salt can exist in the racemic form, in the form of its pure optical isomers, or in the form of a mixture wherein one isomer is enriched relative to the other. In particular, in accordance with the present invention, when the inventive compounds have a single asymmetric carbon atom, the inventive compounds may exist as racemates, that is as mixtures of equal amounts of optical isomers, that is equal amounts of two enantiomers, or in the form of a single enantiomer. As used herein, "single enantiomer" is intended to include a compound that comprises more than 50% of a single enantiomer (that is enantiomeric excess up to 100% pure enantiomer).

When the compound or salt has more than one chiral center, the compound or salt can therefore exist as a mixture of diastereomers or in the form of a single diastereomer. As used herein, "single diastereomer" is intended to mean a compound that comprises more than 50% of a single diastereomer (that is diastereomeric excess to 100% pure diastereomer).

Synthetic Method

A general synthesis of embodiments of the compounds of the invention is depicted in Scheme 1. The synthesis of the compound 104 commences with reaction of alpha hydroxyketone 100 with a primary amine in the presence of catalytic zinc chloride to give the alpha aminoketone 101, which is not isolated but reacts directly with malononitrile to give aminopyrrole 102. Reaction of aminopyrrole 102 with triethyl orthoformate gives the imidate 103. Reaction of imidate 103 with primary amine $R^1NH_2$ in a solvent such as methanol provides final product 104.

Scheme 1

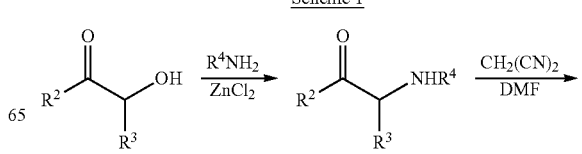

-continued

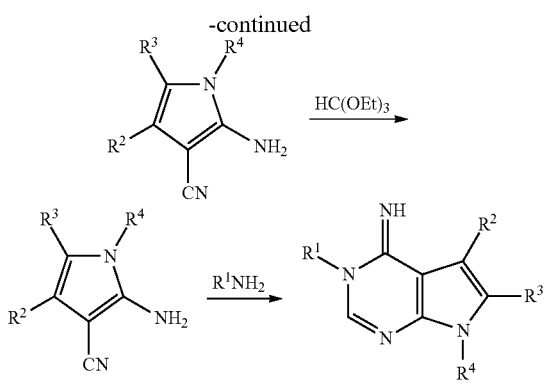

The present invention is further directed to a pharmaceutical composition comprising a pharmaceutically acceptable carrier and at least one compound or salt described herein.

It is preferred that the pharmaceutically acceptable carrier be one that is chemically inert to the active compounds and one that has no detrimental side effects or toxicity under the conditions of use.

The choice of carrier will be determined in part by the particular compound of the present invention chosen, as well as by the particular method used to administer the composition. Accordingly, there is a wide variety of suitable formulations of the pharmaceutical composition of the present invention. The following formulations for oral, aerosol, nasal, pulmonary, parenteral, subcutaneous, intravenous, intramuscular, intraperitoneal, intrathecal, intratumoral, topical, rectal, and vaginal administration are merely exemplary and are in no way limiting.

The pharmaceutical composition can be administered parenterally, such as intravenously, subcutaneously, intradermally, or intramuscularly. Thus, the invention provides compositions for parenteral administration that comprise a solution or suspension of the inventive compound or salt dissolved or suspended in an acceptable carrier suitable for parenteral administration, including aqueous and non-aqueous isotonic sterile injection solutions.

Overall, the requirements for effective pharmaceutical carriers for parenteral compositions are well known to those of ordinary skill in the art. See, such as Banker and Chalmers, eds., *Pharmaceutics and Pharmacy Practice*, J. B. Lippincott Company, Philadelphia, pp. 238-250 (1982), and Toissel, *ASHP Handbook on Injectable Drugs*, 4th ed., pp. 622-630 (1986). Such solutions can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound or salt of the present invention may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-beta-aminopropionates, and 2-alkyl-imidazoline quaternary ammonium salts, and (e) mixtures thereof.

The parenteral formulations can contain preservatives and buffers. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Topical formulations, including those that are useful for transdermal drug release, are well-known to those of skill in the art and are suitable in the context of the invention for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

Formulations suitable for oral administration can consist of (a) liquid solutions, such as a therapeutically effective amount of the inventive compound dissolved in diluents, such as water, saline, or orange juice, (b) capsules, sachets, tablets, lozenges, and troches, each containing a predetermined amount of the active ingredient, as solids or granules, (c) powders, (d) suspensions in an appropriate liquid, and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compound or salt of the present invention, alone or in combination with other suitable components, can be made into aerosol formulations to be administered via inhalation. The compounds are preferably supplied in finely divided form along with a surfactant and propellant. Typical percentages of active compound are 0.01%-20% by weight, preferably 1%-10%. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25%-5%. The balance of the composition is ordinarily propellant. A carrier can also be included as desired, such as lecithin for intranasal delivery. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Additionally, the compound or salt of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

It will be appreciated by one of ordinary skill in the art that, in addition to the aforedescribed pharmaceutical compositions, the compound or salt of the present invention may be formulated as inclusion complexes, such as cyclodextrin inclusion complexes, or liposomes. Liposomes serve to target the compounds to a particular tissue, such as lymphoid tissue or cancerous hepatic cells. Liposomes can also be used to increase the half-life of the inventive compound. Liposomes useful in the present invention include emulsions, foams, micelles, insoluble monolayers, liquid crystals, phospholipid dispersions, lamellar layers and the like. In these preparations, the active agent to be delivered is incorporated as part of a liposome, alone or in conjunction with a suitable chemotherapeutic agent. Thus, liposomes filled with a desired inventive compound or salt thereof, can be directed to the site of a specific tissue type, hepatic cells, for example, where the liposomes then deliver the selected compositions. Liposomes for use in the invention are formed from standard vesicle-forming lipids, which generally include neutral and negatively charged phospholipids and a sterol, such as cholesterol. The selection of lipids is generally guided by consideration of for example, liposome size and stability of the liposomes in the blood stream. A variety of methods are available for preparing liposomes, as described in, for example, Szoka et al., *Ann. Rev. Biophys. Bioeng.,* 9, 467 (1980), and U.S. Pat. Nos. 4,235,871, 4,501,728, 4,837,028, and 5,019,369. For targeting to the cells of a particular tissue type, a ligand to be incorporated into the liposome can include, for example, antibodies or fragments thereof specific for cell surface determinants of the targeted tissue type. A liposome suspension containing a compound or salt of the present invention may be administered intravenously, locally, topically, etc. in a dose that varies according to the mode of administration, the agent being delivered, and the stage of disease being treated.

The perinucleolar compartment (PNC) is a subnuclear body dynamic structure, highly enriched in RNA-binding proteins and pol III RNA, which has been associated with malignancy both in vitro and in vivo. In addition, its presence positively correlates with metastatic capacity, making it a potential marker for cancer development and prognosis vivo (Pollock, C. et al., *Cold Spring Harb Perspect Biol.,* 2010; 2(2), 1-10; Slusarczyk, A. et al., *Cold Spring Harb Symp Quant Biol.* 2010, 75, 599-605).

Although the precise function of the PNC remains to be identified, PNC formation is closely associated with the metastatic phenotype. Notably, solid tumor cell lines seem to have a higher PNC population. A striking observation is the difference in PNC population between metastatically transformed cell lines and their parental counterparts. This observation particularly holds for the PC-3M cell line that was created by removing and culturing a metastatic lesion after implantation of the human prostrate tumor PC-3 cell line in nude mice. PNC prevalence (the percentage of cells with at least one PNC) increases in parallel with disease progression (staging and grading) for breast, ovarian, and colorectal cancers and reaches near 100% in distant metastases. A high PNC prevalence in early stage of breast cancer associates with poor patient outcomes (Kamath, R. V. et al., *Cancer Res.,* 2005, 65(1), 246-53). In addition, PNC prevalence directly correlates with the levels of metastatic capacity in mouse metastasis models of human cancer cells.

PNCs are not associated with traits that are common in both cancer and normal cells, such as proliferation, glycolysis, and differentiation states. The selective association with metastasis makes PNC an ideal and simple marker that reflects the complex trait of cellular malignancy. Thus, PNC reduction can be used as a phenotypic change to identify novel compounds that may not directly target the PNC structure itself, but induce desired changes that lead to the inhibition of cellular malignancy.

Previous studies have shown that classical antitumoral agents, such as topoisomearse I and II inhibitors, DNA cross linkers, a subset of nucleoside analogs, and methotrexate, cause reduction of PNC prevalence (Jin, Y. et al, *Chem Biol.*, 2002, 9, 157-62; Norton, J. T. et al., *Anti-Cancer Drugs.* 2008, 19(1), 23-36; Norton, J. T. et al., *J. Biol. Chem.* 2009, 284, 4090-4101). It has also been shown that the reduction of PNC by these agents is not a non-specific cytotoxic effect but a result of inhibition of the molecular target. This is exemplified by DNA alkylators, microtubule disrupting drugs, hydoxyurea and some nucleoside analogs which are cytotoxic agents that do not disrupt the PNC. Mechanistically it has also been suggested that those drugs which induce PNC reduction may be causing it via DNA damage. To that end, the DNA might serve as a locus for the nucleation of the PNC and this notion is also supported by the fact that the PNC is a heritable trait. However all the agents that are known to reduce PNC have known mechanisms of inducing cytotoxicity, making it difficult to separate an anti-metastic effect from cell death.

The invention further provides a method for treating cancer. The method comprises administering an effective amount of the compound of the invention to an animal afflicted therewith. Preferably, the animal is a mammal. More preferably, the mammal is a human.

The term "mammal" includes, but is not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simioids (monkeys) or of the order Anthropoids (humans and apes). An especially preferred mammal is the human. Furthermore, the subject can be the unborn offspring of any of the forgoing hosts, especially mammals (such as, humans), in which case any screening of the subject or cells of the subject, or administration of compounds to the subject or cells of the subject, can be performed in utero.

In accordance with an embodiment, the invention provides a method of treating or preventing cancer comprising administering to a patient in need thereof a therapeutically effective amount of a compound represented by Formula I, or a pharmaceutically acceptable salt thereof. The cancer can be any suitable cancer responsive to reduction of PNC prevalence, for example, cancers in which PNCs are prevalent.

In accordance with another embodiment, the invention provides a method of treating cancer. The cancer can be any suitable cancer. Preferably, the cancer is a metastatic cancer. For example, the cancer may be adrenocortical carcinoma, AIDS-related lymphoma, AIDS-related malignancies, anal cancer, cerebellar astrocytoma, extrahepatic bile duct cancer, bladder cancer, osteosarcoma/malignant fibrous histiocytoma, brain stem glioma, ependymoma, visual pathway and hypothalamic gliomas, breast cancer, bronchial adenomas/carcinoids, carcinoid tumors, gastrointestinal carcinoid tumors, carcinoma, adrenocortical, islet cell carcinoma, primary central nervous system lymphoma, cerebellar astrocytoma, cervical cancer, chronic lymphocytic leukemia, chronic myelogenous leukemia, clear cell sarcoma of tendon sheaths, colon cancer, colorectal cancer, cutaneous t-cell lymphoma, endometrial cancer, ependymoma, esophageal cancer, Ewing's sarcoma/family of tumors, extracranial germ cell tumors, extragonadal germ cell tumors, extrahepatic bile duct cancer, eye cancers, including intraocular melanoma, and retinoblastoma, gallbladder cancer, gastrointestinal carcinoid tumor, ovarian germ cell tumor, gestational trophoblastic tumor, hairy cell leukemia, head and neck cancer, Hodgkin's disease, hypopharyngeal cancer, hypothalamic and visual pathway glioma, intraocular melanoma, Kaposi's sarcoma, laryngeal cancer, acute lymphoblastic leukemia, acute myeloid leukemia, liver cancer, non-small cell lung cancer, small cell lung cancer, non-Hodgkin's lymphoma, Waldenstrom's macroglobulinemia, malignant mesothelioma, malignant thymoma, medulloblastoma, melanoma, intraocular melanoma, merkel cell carcinoma, metastatic squamous neck cancer with occult primary, multiple endocrine neoplasia syndrome, multiple myeloma/plasma cell neoplasm, mycosis fungoides, myelodysplastic syndrome, chronic myelogenous leukemia, myeloid leukemia, multiple myeloma, myeloproliferative disorders, nasal cavity and paranasal sinus cancer, nasopharyngeal cancer, neuroblastoma, oral cancer, oral cavity and lip cancer, oropharyngeal cancer, osteosarcoma/malignant fibrous histiocytoma of bone, ovarian cancer, ovarian low malignant potential tumor, pancreatic cancer, paranasal sinus and nasal cavity cancer, parathyroid cancer, penile cancer, pheochromocytoma, pituitary tumor, pleuropulmonary blastoma, prostate cancer, rectal cancer, renal cell (kidney) cancer, transitional cell cancer (such as renal pelvis and ureter), retinoblastoma, rhabdomyosarcoma, salivary gland cancer, malignant fibrous histiocytoma of bone, soft tissue sarcoma, sezary syndrome, skin cancer, small intestine cancer, stomach (gastric) cancer, supratentorial primitive neuroectodermal and pineal tumors, cutaneous T-cell lymphoma, testicular cancer, malignant thymoma, thyroid cancer, gestational trophoblastic tumor, urethral cancer, uterine sarcoma, vaginal cancer, vulvar cancer, and Wilms' tumor.

In any of the embodiments of the invention, the cancer can be any cancer in any organ, for example, a cancer is selected from the group consisting of brain carcinoma, glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, anaplastic large-cell lymphoma, leukemia, multiple myeloma, mesothelioma, and melanoma, and combinations thereof.

In an embodiment, the metastatic cancer is selected from the group consisting of breast cancer, ovarian cancer, colorectal cancer, brain cancer, and prostate cancer.

In accordance with other embodiments, the invention provides a method of potentiating or enhancing anticancer activity of an anticancer agent, the method comprising coadministering to a patient in need thereof an effective amount of an anticancer agent and a compound or salt of the invention. The anticancer agent can be chosen from reversible DNA binders, DNA alkylators, and DNA strand breakers.

Examples of suitable reversible DNA binders include topetecan hydrochloride, irinotecan (CPT11-Camptosar), rubitecan, exatecan, nalidixic acid, TAS-103, etoposide, acridines (such as amsacrine, aminocrine), actinomycins (such as actinomycin D), anthracyclines (such as doxorubicin, daunorubicin), benzophenainse, XR 11576/MLN 576, benzopyridoindoles, Mitoxantrone, AQ4, Etopside, Teniposide, (epipodophyllotoxins), and bisintercalating agents such as triostin A and echinomycin.

Examples of suitable DNA alkylators include sulfur mustard, the nitrogen mustards (such as mechlorethamine), chlorambucil, melphalan, ethyleneimines (such as triethylenemelamine, carboquone, diaziquone), methyl methanesulfonate, busulfan, CC-1065, duocaimycins (such as duocarmycin A, duocarmycin SA), metabolically activated alkylating agents such as nitrosoureas (such as carmustine, lomustine, (2-chloroethyl)nitrosoureas), triazne antitumor drugs such as triazenoimidazole (such as dacarbazine), mitomycin C, leinamycin, and the like.

Examples of suitable DNA strand breakers include doxorubicin and daunorubicin (which are also reversible DNA binders), other anthracyclines, bleomycins, tirapazamine, enediyne antitumor antibiotics such as neocarzinostatin, esperamicins, calicheamicins, dynemicin A, hedarcidin, C-1027, N1999A2, esperamicins, zinostatin, and the like.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. Treatment of cancer can be evidenced, for example, by a reduction in tumor size, a reduction in tumor burden, a reduction in clinical symptoms resulting from the cancer, increase in longevity, increase in tumor free survival time, and the like. Treating in embodiments, can include inhibiting the development or progression of a cancer or metastatic cancer.

By the term "coadminister" is meant that each of the at least two compounds be administered during a time frame wherein the respective periods of biological activity overlap. Thus, the term includes sequential as well as coextensive administration of two or more drug compounds. The compounds can be administered simultaneously, separately (chronologically staggered), cyclically, or sequentially and in any order, such as before or after.

One skilled in the art will appreciate that suitable methods of utilizing a compound and administering it to a human for the treatment or prevention of disease states, in particular, cancer, which would be useful in the method of the present invention, are available. Although more than one route can be used to administer a particular compound, a particular route can provide a more immediate and more effective reaction than another route. Accordingly, the described methods are merely exemplary and are in no way limiting.

The dose administered to a mammal, particularly, a human, in accordance with the present invention should be sufficient to effect the desired response. Such responses include reversal or prevention of the adverse effects of the disease for which treatment is desired or to elicit the desired benefit. One skilled in the art will recognize that dosage will depend upon a variety of factors, including the age, condition, and body weight of the human, as well as the source, particular type of the disease, and extent of the disease in the human. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states may require prolonged treatment involving multiple administrations.

Suitable doses and dosage regimens can be determined by conventional range-finding techniques known to those of ordinary skill in the art. Generally, treatment is initiated with smaller dosages that are less than the optimum dose of the compound. Thereafter, the dosage is increased by small increments until the optimum effect under the circumstances is reached. The present inventive method typically will involve the administration of about 0.1 to about 300 mg of one or more of the compounds described above per kg body weight of the animal or mammal.

The therapeutically effective amount of the compound or compounds administered can vary depending upon the desired effects and the factors noted above. Typically, dosages will be between 0.01 mg/kg and 250 mg/kg of the subject's body weight, and more typically between about 0.05 mg/kg and 100 mg/kg, such as from about 0.2 to about 80 mg/kg, from about 5 to about 40 mg/kg or from about 10 to about 30 mg/kg of the subject's body weight. Thus, unit dosage forms can be formulated based upon the suitable ranges recited above and the subject's body weight. The term "unit dosage form" as used herein refers to a physically discrete unit of therapeutic agent appropriate for the subject to be treated.

Alternatively, dosages are calculated based on body surface area and from about 1 mg/m$^2$ to about 200 mg/m$^2$, such as from about 5 mg/m$^2$ to about 100 mg/m$^2$ will be administered to the subject per day. In particular embodiments, administration of the therapeutically effective amount of the compound or compounds involves administering to the subject from about 5 mg/m$^2$ to about 50 mg/m$^2$, such as from about 10 mg/m$^2$ to about 40 mg/m$^2$ per day. It is currently believed that a single dosage of the compound or compounds is suitable, however a therapeutically effective dosage can be supplied over an extended period of time or in multiple doses per day. Thus, unit dosage forms also can be calculated using a subject's body surface area based on the suitable ranges recited above and the desired dosing schedule.

In accordance with other embodiments, the invention provides a method of potentiating or enhancing anticancer activity of radiation treatment, the method comprising coadministering to a patient in need thereof an effective amount of a radiation treatment and a compound or salt of the invention. The radiation treatment can be any suitable radiation treatment used in the treatment of cancers.

The invention further provides a use of a compound or salt of the invention in the manufacture of a medicament for treating or preventing cancer. The medicament typically is a pharmaceutical composition as described herein.

The following examples further illustrate the invention but, of course, should not be construed as in any way limiting its scope.

EXAMPLES

General Chemistry. Reagents and solvents used were commercial anhydrous grade and used without further purification. Column chromatography was carried out over silica gel (100-200 mesh). $^1$H NMR spectra were recorded with a Bruker 400 MHz spectrometer from solutions in CDCl$_3$ and DMSO-d6. Chemical shifts in $^1$H NMR spectra are reported in parts per million (ppm, δ) downfield from the internal standard Me$_4$Si (TMS, δ=0 ppm). Chemical shifts in $^{13}$C NMR spectra are reported in parts per million (ppm, δ) calibrated from residual CHCl$_3$ (δ=77.0 ppm) signal and are reported using an APT pulse sequence displaying methyl and methine (CH$_3$ and CH) signals as down and quaternary and methylene (C and CH$_2$) signals as up. Molecular weight confirmation was performed using an Agilent 6224 Time-Of-Flight Mass Spectrometer (TOF, Agilent Technologies, Santa Clara, Calif.). A 3 minute gradient from 5 to 100% Acetonitrile in water (0.03% formic acid) was used with a 5.1 minute run time at a flow rate of 0.4 mL/min. A Waters Atlantis T3 C18 column (1.8 micron, 2.1×50 mm) was used at a temperature of 25° C. Confirmation of molecular formula was confirmed using electrospray ionization in the positive mode with the Agilent Masshunter software (version B.02).

Example 1

This Example illustrates a procedure for the synthesis of 2-Amino-1-benzyl-4,5-diphenyl-1H-pyrrole-3-carbonitrile A, an intermediate in the synthesis of a compound in accordance with an embodiment of the invention.

A modified Voigt reaction/Knoevenagel condensation sequence was carried out using the procedure described in Roth, H. J. et al., *Arch. Pharmaz.* 1975, 308, 179-185. Benzoin (2.19 g, 10.3 mmol), benzylamine (1.66 g, 15.5 mmol, 1.5 equiv.), and zinc chloride (0.10 g, 0.73 mmol, 0.07 equiv.) were heated at reflux for 3 hours and the mixture was removed from the oil bath. To the still warm mixture was added malononitrile (1.35 g, 20.64 mmol, 2.0 equiv.) in DMF (3 mL). The reaction mixture was allowed to cool to room temperature and stirred for 16 hrs, affording the crude pyrrole as a dark brown solid. The solid was partitioned between water and CH$_2$Cl$_2$ and the aqueous extracted with additional CH$_2$Cl$_2$ (2×50 mL). The combined organics were dried with Na$_2$SO$_4$ and the solvent removed in vacuo to afford the previously reported pyrrole product A as a light brown solid (1.67 g, 4.78 mmol, 46% yield), which was used without further purification. R$_f$=0.22 (20% EtOAc in hexanes); $^1$H NMR δ 4.91 (s, 2 H), 7.06-7.37 (complex, 15 H); $^{13}$C NMR δ d (CH, CH$_3$) 125.8 (×2), 126.3, 127.9, 128.1, 128.2 (×2), 128.6 (×2), 128.7 (×2), 129.2 (×2), 131.0; u (C, CH$_2$) 46.9, 117.5, 120.9, 125.6, 130.8, 133.1, 136.0, 146.0, 162.5; IR 3329, 3228, 3031, 2195, 1663, 1556 cm$^{-1}$; HRMS calcd for C$_{24}$H$_{20}$N$_3$ [M+H$^+$] 350.1657, found 350.1648.

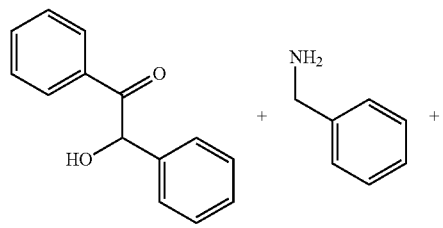

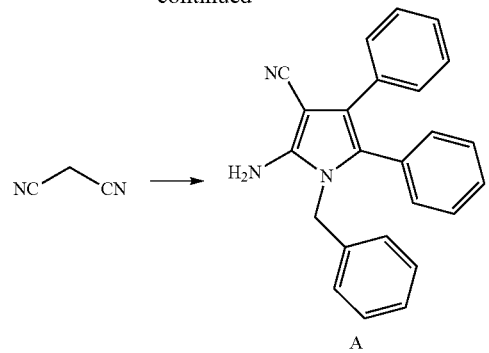

A

Example 2

This Example illustrates a procedure for the synthesis of (E)-Ethyl N-(1-benzyl-3-cyano-4,5-diphenyl-1H-pyrrol-2-yl)formimidate B, an intermediate in the synthesis of a compound in accordance with an embodiment of the invention.

2-Amino-1-benzyl-4,5-diphenyl-1H-pyrrole-3-carbonitrile A (1.07 g, 3.06 mmol) and triethylorthoformate (4.54 g, 30.6 mmol, 10 equiv.) were heated at 75° C. for 14 hrs and the excess triethylorthoformate was removed in vacuo. The residue was dissolved in a minimum of CH$_2$Cl$_2$, adsorbed onto celite, and chromatographed on silica to afford the formimidate product B as a tan solid (0.80 g, 1.97 mmol, 64% yield). R$_f$=0.47 (20% EtOAc in hexanes); mp=154-156° C.; $^1$H NMR δ 1.30 (t, J=7.2 Hz, 3 H), 4.27 (dq, J=0.8, 8.2 Hz, 2 H), 5.05 (s, 2 H), 6.86 (dd, J=2.0, 8.0 Hz, 2 H), 7.06 (dd, J=1.6, 8.0 Hz, 2 H), 7.14-7.29 (complex, 11 H), 8.51 (s, 1 H); $^{13}$C NMR δ d (CH, CH$_3$) 13.9, 126.4 (×2), 126.5, 127.2, 128.1 (×2), 128.2, 128.4 (×4), 129.0 (×2), 131.2 (×2), 158.3; u (C, CH$_2$) 46.9, 63.2, 117.9, 123.1, 128.5, 130.8, 132.8, 137.6, 143.9; IR 2208, 1627, 1605 cm$^{-1}$; HRMS calcd for C$_{27}$H$_{24}$N$_3$O [M+H$^+$] 406.1919, found 406.1915.

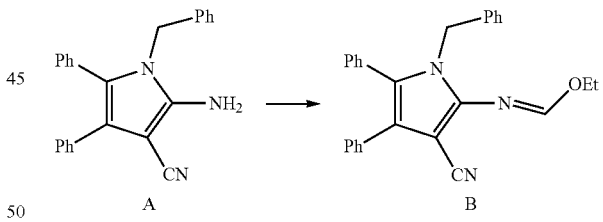

Example 3

This Example illustrates a synthesis of a compound in accordance with an embodiment of the invention, trans-4-(7-Benzyl-4-imino-5,6-diphenyl-4,7-dihydro-3H-pyrrolo[2,3-d]pyrimidin-3-yl)cyclohexanol 2.

A solution of the formimidate B (40 mg, 0.099 mmol) and trans-4-aminocyclohexanol hydrochloride (23 mg, 0.15 mmol, 1.5 equiv) in MeOH (1.5 mL) were heated in a reaction vial at 60° C. for 17 hrs then cooled to room temperature. Evaporation of the solvent and purification of the residue by mass-directed preparative reverse-phase HPLC afforded the pyrolopyrimidine product 2 as a tan solid (16 mg, 0.034 mmol, 34% yield). R$_f$=0.39 (1:1 acetone: CH$_2$Cl$_2$ with 1% Et$_3$N); mp=171-185° C.; $^1$H NMR δ 1.66

(m, 4 H), 2.13 (d, J=8.8 Hz, 4 H), 3.70 (m, 1 H), 5.14 (m, 1 H), 5.28 (s, 2 H), 6.45 (br s, 1 H), 6.95 (m, 2 H), 7.04 (d, J=6.8 Hz, 2 H), 7.18-7.26 (complex, 11 H), 7.80 (s, 1 H); $^{13}$C NMR δ d (CH, CH$_3$) 52.0, 69.7, 126.7 (×2), 126.9, 127.3, 128.0, 128.1 (×2), 128.3 (×2), 128.4 (×2), 130.5 (×2), 131.0 (×2), 142.3; u (C, CH$_2$) 30.6, 34.7, 46.0, 102.9, 118.1, 130.4, 133.2, 133.6, 137.7, 142.5, 155.1; IR 1625, 1604 cm$^{-1}$; HRMS calcd for C$_{31}$H$_{31}$N$_4$O [M+H$^+$] 475.2498, found 475.2492.

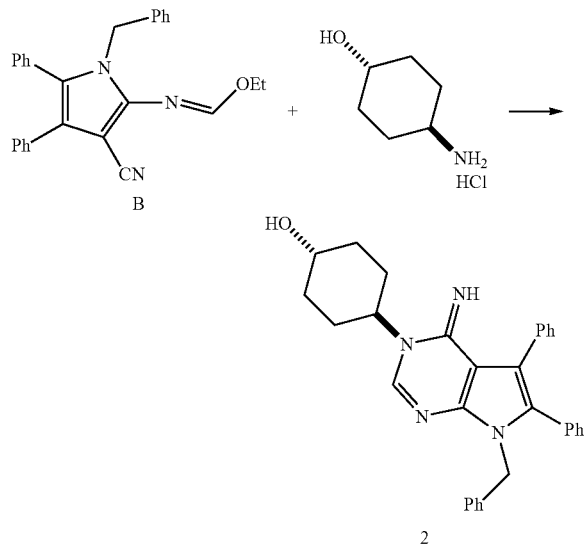

Example 4

This Example illustrates a procedure for the synthesis of 2-amino-1-phenethyl-4,5-diphenyl-1H-pyrrole-3-carbonitrile C, an intermediate in the synthesis of a compound in accordance with an embodiment of the invention.

Benzoin (4.35 g, 20.5 mmol), phenethylamine (3.73 g, 30.7 mmol), and zinc chloride (0.10 g, 0.73 mmol, 0.07 equiv.) were heated at reflux for 3 hours and the mixture was removed from the oil bath. To the still warm mixture malononitrile (2.71 g, 41.0 mmol, 2.0 equiv.) in DMF (3 mL) was added. The reaction mixture was allowed to cool to room temperature and stirred for 16 hrs, affording the crude pyrrole as a dark brown solid. The solid was partitioned between water and CH$_2$Cl$_2$ and the aqueous extracted with additional CH$_2$Cl$_2$ (2×50 mL). The combined organics were dried with Na$_2$SO$_4$ and the solvent removed in vacuo to afford pyrrole product C (3.50 g, 9.63 mmol, 47% yield) as a light brown solid. R$_f$=0.13 (20% EtOAc in hexanes); mp=144-149° C.; IR 3330, 2199, 1634, 1601, 1502 cm$^{-1}$; HRMS calcd for C$_{25}$H$_{23}$N$_3$ [M H$^+$] 364.1814, found 364.1827.

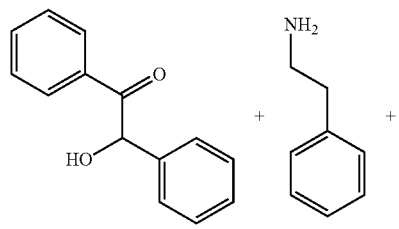

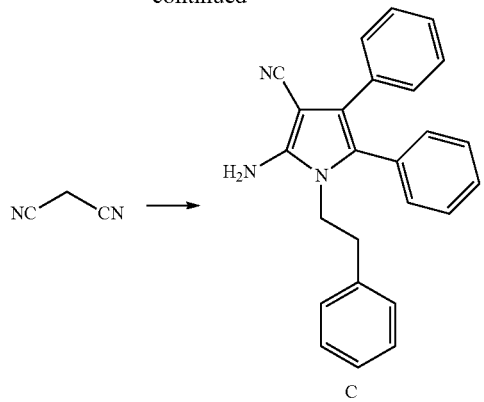

Example 5

This example demonstrates a high content assay for PNC detection.

The quantitative output for this assay is the reduction of PNC prevalence. The PNC can be detected in living cells by the expression of a green fluorescent protein (GFP) tagged to the PNC localized protein, PTB. A PC3M cell line was used that stably expresses GFP-PTB to mark PNCs. This method eliminates the need for immunofluorescent staining. Previous studies demonstrate that the fusion proteins behave similarly to their endogenous counterparts: transient and stable over-expression of the fusion protein did not have detectable adverse effects on cell morphology or cell growth. After treatment, cells are fixed and the nuclei are counter-stained with Hoechst 33342 dye; the cells are then ready for analysis.

The IN Cell Analyzer 1000 automated fluorescent imaging system (GE Healthcare, Piscataway, N.J.) was used for automated image acquisition. Images were acquired with a 20× objective using a 475/20 nm excitation filter, a 535/50 nm HQ emission filter, a Q505LP dichroic filter, and an exposure time of 100 to 150 ms (adjusted to obtain a dynamic range of ~200 to 1750), with no camera binning. The instrument acquired images of each well in a 1536-well plate with a laser-based autofocus system. To score PNC prevalence in a high-content throughput, the Multi-Target Analysis (MTA) algorithm (GE Healthcare, Investigator v3.5) to identify individual cells and granules (PNCs) within these cells was used. The nucleus was segmented via a region growing method (50 μm$^2$ minimum area) with light shading and noise removal to allow "touching" nuclei to be separated. Granules in the nucleus (PNCs) were segmented using a multiscale top hat method, which measures granules of 1 to 2 μm in size and used a smart masking method to identify the boundaries of each segmented granule. The algorithm was optimized and validated using positive and negative controls (50 μM camptothecin and DMSO, respectively). In particular, the MTA algorithm allows for the identification of multiple subcellular compartments and organelles (or granules) within those compartments. In this instance, the algorithm's capability to identify objects within the same color channel that only differ in size or fluorescent intensity was utilized. Also, the algorithm allows for building complex hierarchical classification systems, using output measures within the algorithm to filter and define subpopulations. For this particular assay, PNC-positive cells were scored when 1 to 3 PNC granules were detected per nucleus.

Cells that contained 0 granules were scored as PNC negative, and cells with >3 granules were assumed to be false positives (very few cells have more than 3 PNCs in one focus plane), and were also scored as PNC negative. The assay was conducted using the sequence set forth in Table 1.

TABLE 1

| Sequence | Value | Parameter | Description |
|---|---|---|---|
| 1 | Cells | 5 µL | 750-1000 cells/well |
| 2 | Time | 4 hrs | Incubate at 37° C. and 5% $CO_2$ |
| 3 | Reagent | 23 nL | 0.5 nM to 58 µM final concentrations (in titration) |
| 4 | Time | 16 hrs | Incubate at 37° C. and 5% $CO_2$ |
| 5 | Reagent | 4 µL | Fixation step with 6% EM grade paraformaldehyde and 0.1% Triton X-100 |
| 6 | Time | 20 min | RT incubation |
| 7 | Wash | 5 µL | Liquid was aspirated and 5 µL of PBS was added |
| 8 | Wash | 5 µL | Liquid was aspirated and 5 µL of PBS was added |
| 9 | Reagent | 5 µL | Staining with PBS containing 1 µg/mL Hoechst 33342 |
| 10 | Detector | Fluorescence | IN Cell 1000, 20 x objective |

Example 6

This example demonstrates an adenosine triphosphate (ATP) quantitation assay.

This follow-up assay was conducted to measure the effect of compounds on cell health by measuring ATP levels (ATPLite™). ATPLite™ is an ATP monitoring system based on firefly (*Photinus pyralis*) luciferase. The level of ATP in a metabolically active cell is a general marker for its viability. ATP levels are often reduced during necrosis or apoptosis. In this assay, the luciferase enzyme catalyzes the conversion of the added substrate D-luciferin to oxyluciferin and light with ATP. Thus, the emitted light is proportional to the ATP concentration. For this assay, the highly metastatic PC3M reporter cell line stably expressing the PTB-GFP was provided by Professor Sui Huang of Northwestern University. The media and cell culture reagents were purchased from Invitrogen (Carlsbad, Calif.), ATPLite™ came from PerkinElmer. The assay was conducted using the sequence set forth in Table 2.

TABLE 2

| Sequence | Value | Parameter | Description |
|---|---|---|---|
| 1 | Cells | 5 µL | 2000 cells/well |
| 2 | Time | 4 hrs | Incubate at 37° C. and 5% $CO_2$ |
| 3 | Reagent | 23 nL | 0.5 nM to 58 µM final concentrations (in titration) |
| 4 | Time | 24 hrs | Incubate at 37° C. and 5% $CO_2$ |
| 5 | Reagent | 3 µL | ATPLite |
| 6 | Time | 20 min | RT incubation |
| 7 | Centrifuge | 1 min | 1500 RPM |
| 8 | Detector | Luminescence | ViewLux |

Example 7

This example demonstrates a tumor cell migration assay.

High-content tumor cell migration assays in 3-dimensional extracellular matrices are powerful tools for modeling and understanding the biology of this critical step in the process of metastasis. However, most of the available methods are not amenable to the throughput required by studies of comparative pharmacology or small scale screening. For this reason, compounds were tested in BellBrook Labs™ automated high-content tumor cell invasion assays. A standard screening-sized plate with an array of embedded microchannels was designed and constructed from common thermoplastics.

PC3M cells were tested for invasion through 3D fibrillar collagen in the Iuvo Single Microchannel Plate, in the presence of varying levels of test compounds. Channels were prefilled with 820 nL of 3-dimensional type I collagen at 1 mg/mL, through the input port. Following gelation, 2,000 PC3M cells were seeded into the output port using growth media (RPMI+10% FBS with antibiotics) in a volume of 5 µL. Cells were incubated in a 37° C. incubator inside a humidified container to control evaporation (Bioassay dish, Corning). Media, including test compounds, was changed daily for 5 days. At the end of the assay, cells were fixed and stained with Hoechst 33342, then imaged with 4× objective under epifluorescence. Under these conditions, cells across the 140 µM height range of the microchannel can be reliably identified. Test compounds were serially diluted by a factor of 3 to produce 10 concentrations ranging from 50 or 100 µM to 2.5 nM. All assays were conducted in the presence of 0.1% DMSO. Four replicates were performed for all test concentrations. Each plate had 4 dose response curves, as well as 16 channels with no compound and 16 channels with 50 µM blebbistatin (positive control). Analysis was done by automatically cropping each image at the right edge of the channel and counting cells via the 'count nuclei' function on Metamorph (Molecular Devices). Non-linear regression analysis was performed with Graph-Pad Prism. The results are set forth in Table 3.

TABLE 3

| Compound | PNC $AC_{50}$ (µM) | Invasion cell # $IC_{50}$ (µM) | Proliferation output port $IC_{50}$ (µM) | Comments |
|---|---|---|---|---|
| 2 | 0.40 | 3.16 | 3.98 | embodiment |
| Control | inactive | 79.43 | 19.95 | Negative control |
| 1 | 0.09 | 3.16 | 5.01 | embodiment |

Example 8

This example demonstrates the effect of an embodiment of the invention on colony formation of PC3M cells.

Compound 2 was tested for its ability to affect anchorage independent growth in a soft agar assay, a stringent method to detect malignant transformation of cells in vitro. Compound 2 demonstrated a dose dependent reduction in the number of colonies after 14 days at very low concentrations (3.8, 18.6 nM), with no impact on cell viability. Thus, the compound exhibits potent inhibition of anchorage independent growth in PC3M cells. The left hand side of FIG. 1 illustrates a histogram representing the number and size of PC3M soft agar colonies after 14 days of treatment with compound 2 at two different concentrations. A clear reduction of the number of colonies of PC3M cells was observed, particularly at a compound concentration of 18.6 nM. The right hand side of FIG. 1 illustrates two representative images taken at two different regions of the soft agar medium after treatment with DMSO (vehicle) (top row), compound 2 at 3.8 nM (middle row), and compound 2 at 18.6 nM (bottom row).

Example 9

This example demonstrates biological activities of embodiments of the invention. The high content assay for PNC detection as described in Example 5 was used to provide the PNC $AC_{50}$ results. The ATP quantitation assay as described in Example 6 was used to provide the ATP $AC_{50}$ results. The results are set forth in Table 4.

TABLE 4

| Compound | Structure | PNC $IC_{50}$ (μM) | ATP $IC_{50}$ (μM) |
|---|---|---|---|
| 56 | 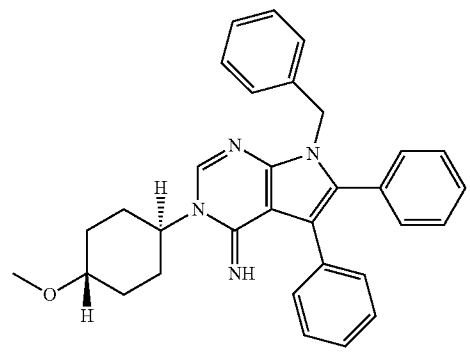 [SMILES: CO[C@H]1CC[C@H](n2cnc3c(c(-c4ccccc4)c(-c4ccccc4)n3Cc3ccccc3)c2=N)CC1] | 0.009 | 19.182 |
| 2 | 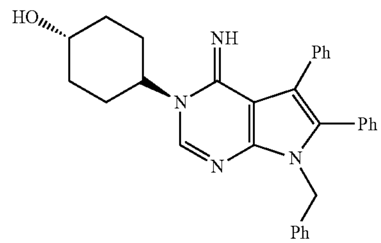 | 0.024 | 19.182 |
| 1 | 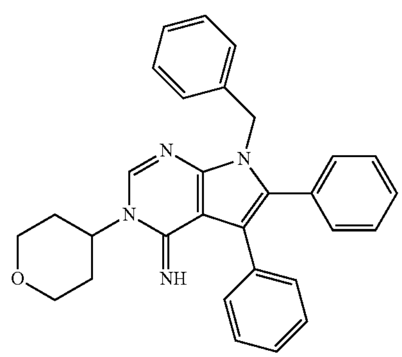 [SMILES: N=c1c2c(-c3ccccc3)c(-c3ccccc3)n(Cc3ccccc3)c2ncn1C1CCOCC1] | 0.030 | 152.369 |
| 3 | 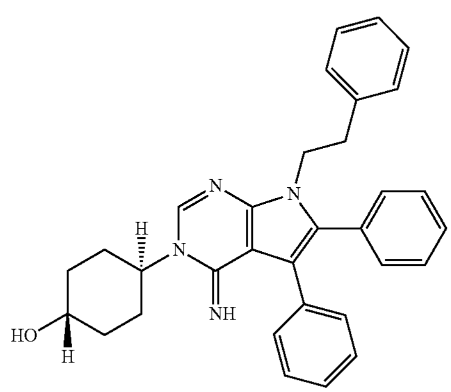 [SMILES: N=c1c2c(-c3ccccc3)c(-c3ccccc3)n(CCc3ccccc3)c2ncn1[C@H]1CC[C@H](O)CC1] | 0.047 | 9.614 |

TABLE 4-continued

| Compound | Structure | PNC IC$_{50}$ (μM) | ATP IC$_{50}$(μM) |
|---|---|---|---|
| 57 | 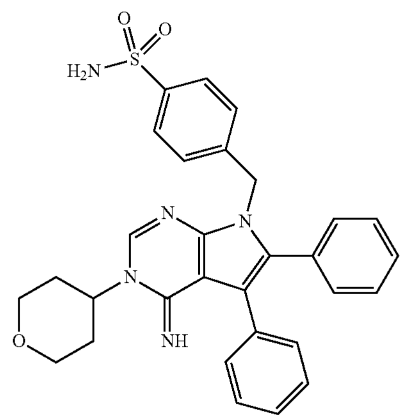 [SMILES: N=c1c2c(-c3ccccc3)c(-c3ccccc3)n(Cc3ccc(S(N)(=O)=O)cc3)c2ncn1C1CCOCC1] | 0.059 | 96.138 |
| 4 | 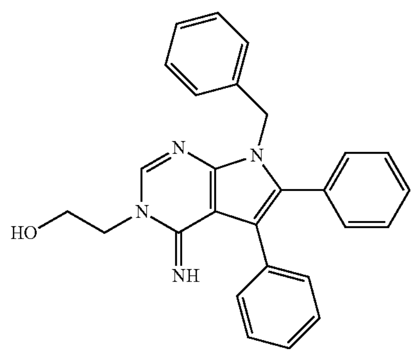 [SMILES: N=c1c2c(-c3ccccc3)c(-c3ccccc3)n(Cc3ccccc3)c2ncn1CCO] | 0.118 | 76.365 |
| 61 | 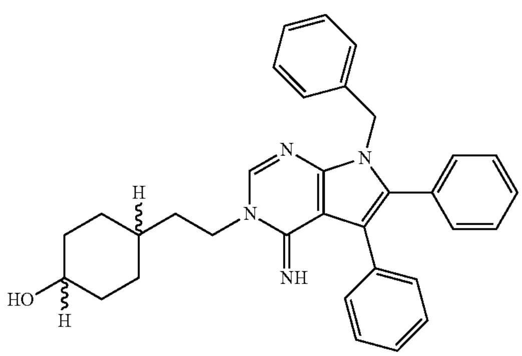 [SMILES: N=c1c2c(-c3ccccc3)c(-c3ccccc3)n(Cc3ccccc3)c2ncn1CCC1CCC(O)CC1] | 0.118 | 24.149 |
| 59 | 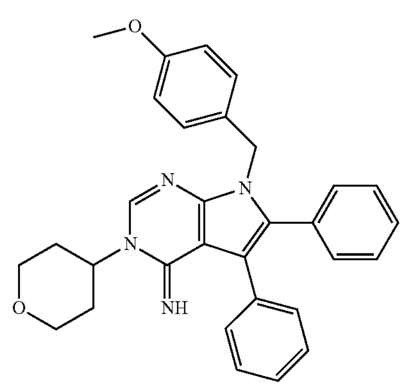 [SMILES: COc1ccc(Cn2c(-c3ccccc3)c(-c3ccccc3)c3c(=N)n(C4CCOCC4)cnc32)cc1] | 0.118 | 24.149 |

TABLE 4-continued

| Compound | Structure | PNC IC$_{50}$ (μM) | ATP IC$_{50}$(μM) |
|---|---|---|---|
| 60 | 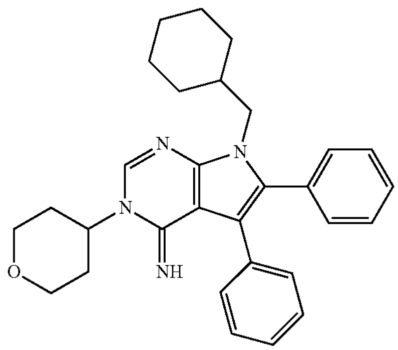 [SMILES: N=c1c2c(-c3ccccc3)c(-c3ccccc3)n(CC3CCCCC3)c2ncn1C1CCOCC1] | 0.118 | 24.149 |
| 58 | 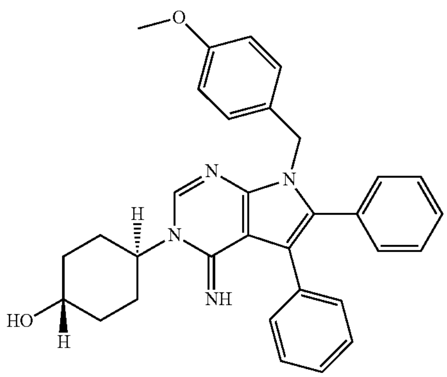 [SMILES: COc1ccc(Cn2c(-c3ccccc3)c(-c3ccccc3)c3c(=N)n([C@H]4CC[C@H](O)CC4)cnc32)cc1] | 0.118 | 24.149 |
| 9 | 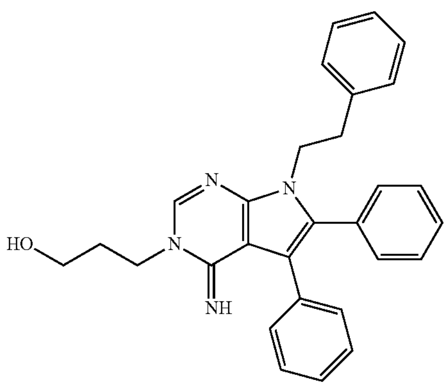 [SMILES: N=c1c2c(-c3ccccc3)c(-c3ccccc3)n(CCc3ccccc3)c2ncn1CCCO] | 0.148 | 19.182 |
| 63 | 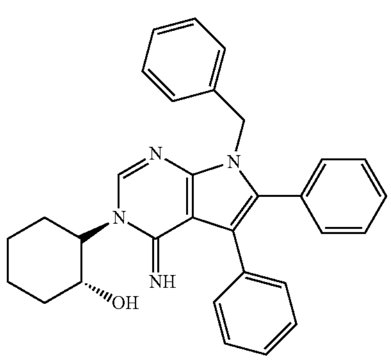 | 0.148 | 19.182 |

TABLE 4-continued

| Compound | Structure | PNC IC$_{50}$ (μM) | ATP IC$_{50}$(μM) |
|---|---|---|---|
| 62 | 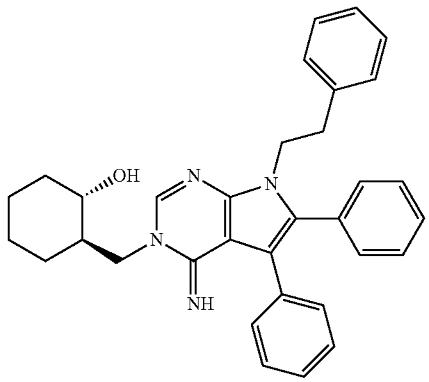 [SMILES: N=c1c2c(-c3ccccc3)c(-c3ccccc3)n(CCc3ccccc3)c2ncn1C[C@H]1CCCC[C@@H]1O] | 0.148 | 24.149 |
| 8 | 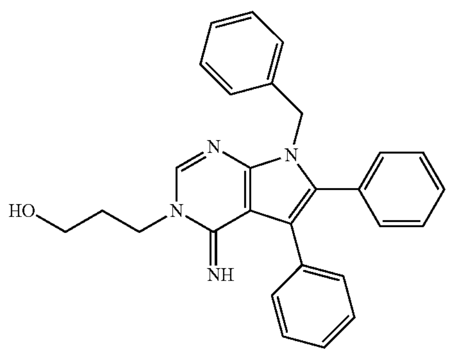 [SMILES: N=c1c2c(-c3ccccc3)c(-c3ccccc3)n(Cc3ccccc3)c2ncn1CCCO] | 0.148 | 24.149 |
| 5 | 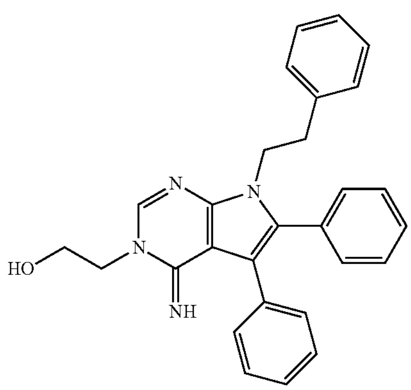 [SMILES: N=c1c2c(-c3ccccc3)c(-c3ccccc3)n(CCc3ccccc3)c2ncn1CCO] | 0.187 | 19.182 |
| 64 | 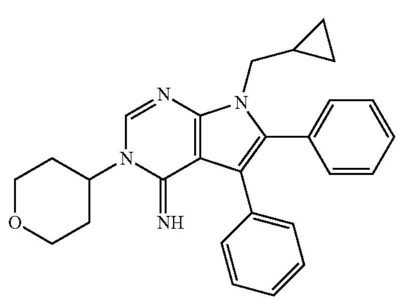 [SMILES: N=c1c2c(-c3ccccc3)c(-c3ccccc3)n(CC3CC3)c2ncn1C1CCOCC1] | 0.187 | 38.273 |

TABLE 4-continued

| Compound | Structure | PNC IC$_{50}$ (μM) | ATP IC$_{50}$ (μM) |
|---|---|---|---|
| 13 | 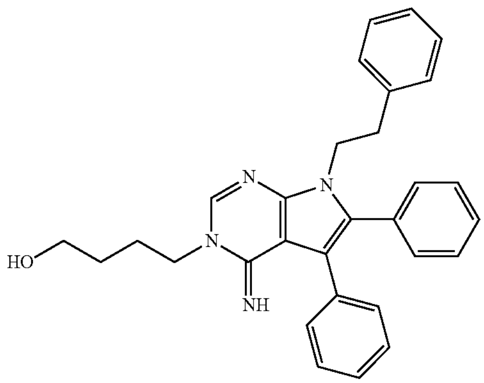 [SMILES: N=c1c2c(-c3ccccc3)c(-c3ccccc3)n(CCc3ccccc3)c2ncn1CCCCO] | 0.235 | 15.237 |
| 65 | 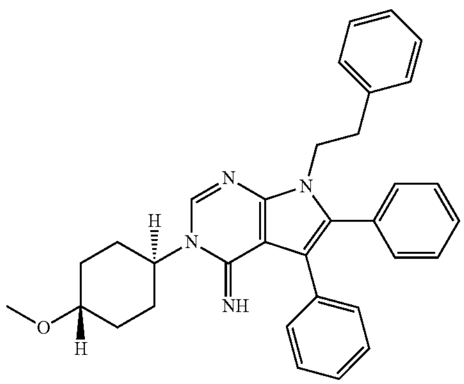 [SMILES: CO[C@H]1CC[C@H](n2cnc3c(c(-c4ccccc4)c(-c4ccccc4)n3CCc3ccccc3)c2=N)CC1] | 0.235 | 19.182 |
| 67 | 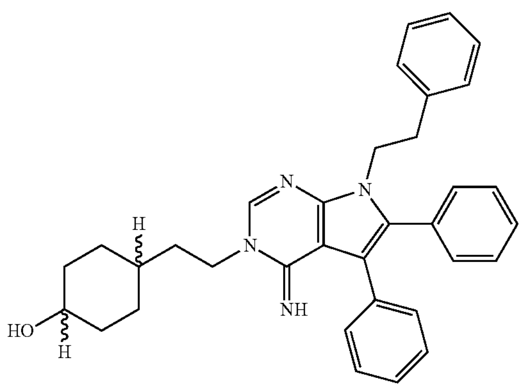 [SMILES: N=c1c2c(-c3ccccc3)c(-c3ccccc3)n(CCc3ccccc3)c2ncn1CCC1CCC(O)CC1] | 0.296 | 24.149 |
| 66 | 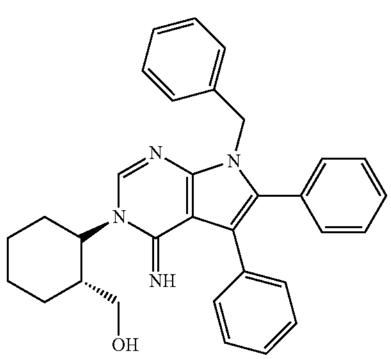 | 0.296 | 76.365 |

TABLE 4-continued

| Compound | Structure | PNC IC$_{50}$ (μM) | ATP IC$_{50}$(μM) |
|---|---|---|---|
| 68 | 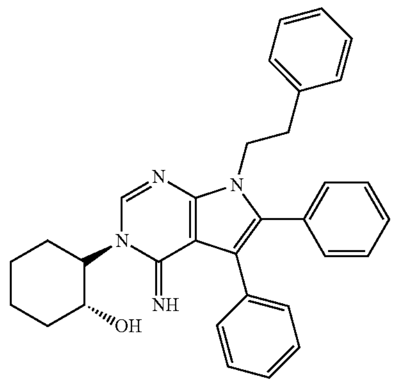 | 0.296 | 38.273 |
| 15 | 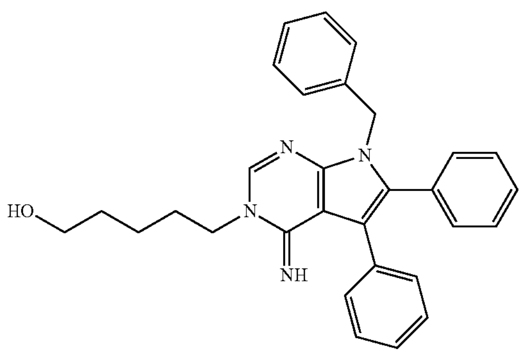 [SMILES: N=c1c2c(-c3ccccc3)c(-c3ccccc3)n(Cc3ccccc3)c2ncn1CCCCCO] | 0.372 | 24.149 |
| 71 | 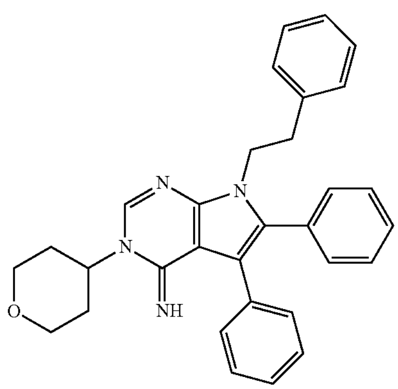 [SMILES: N=c1c2c(-c3ccccc3)c(-c3ccccc3)n(CCc3ccccc3)c2ncn1C1CCOCC1] | 0.372 | 121.031 |
| 70 | 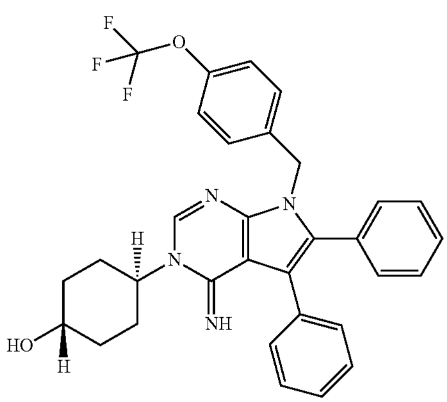 [SMILES: N=c1c2c(-c3ccccc3)c(-c3ccccc3)n(Cc3ccc(OC(F)(F)F)cc3)c2ncn1[C@H]1CC[C@H](O)CC1] | 0.372 | 24.149 |

TABLE 4-continued

| Compound | Structure | PNC IC$_{50}$ (μM) | ATP IC$_{50}$(μM) |
|---|---|---|---|
| 69 | 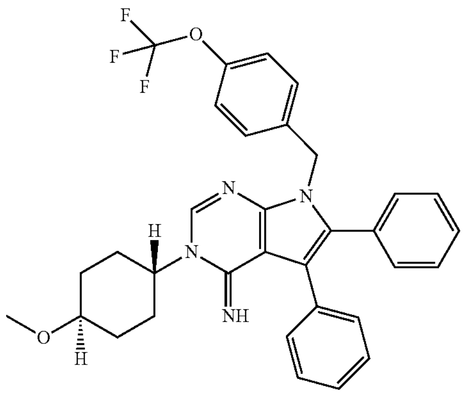 [SMILES: CO[C@H]1CC[C@H](n2cnc3c(c(-c4ccccc4)c(-c4ccccc4)n3Cc3ccc(OC(F)(F)F)cc3)c2=N)CC1] | 0.372 | 19.182 |
| 72 | 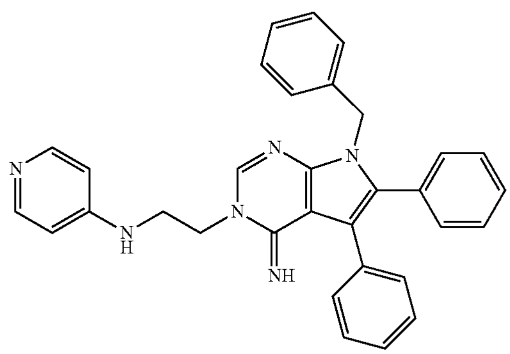 [SMILES: N=c1c2c(-c3ccccc3)c(-c3ccccc3)n(Cc3ccccc3)c2ncn1CCNc1ccncc1] | 0.469 | 24.149 |
| 20 | 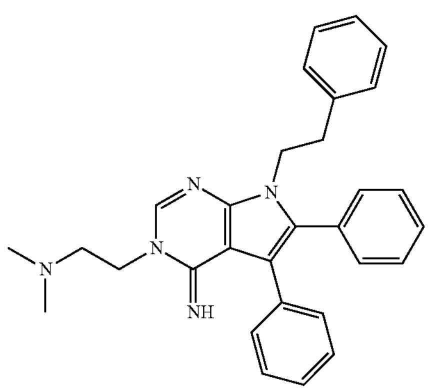 [SMILES: CN(C)CCn1cnc2c(c(-c3ccccc3)c(-c3ccccc3)n2CCc2ccccc2)c1=N] | 0.469 | 96.138 |
| 16 | 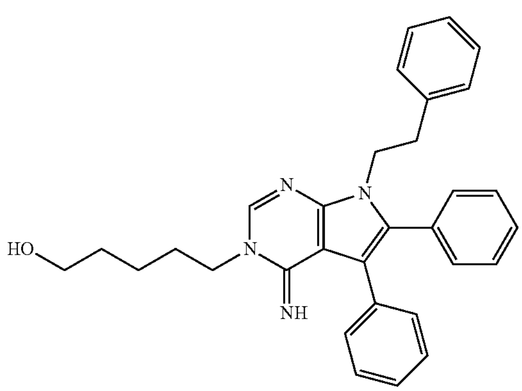 [SMILES: N=c1c2c(-c3ccccc3)c(-c3ccccc3)n(CCc3ccccc3)c2ncn1CCCCCO] | 0.590 | 38.273 |

TABLE 4-continued

| Compound | Structure | PNC IC$_{50}$ (μM) | ATP IC$_{50}$(μM) |
|---|---|---|---|
| 73 | 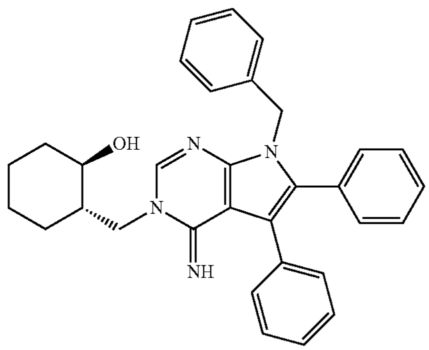 [SMILES: N=c1c2c(-c3ccccc3)c(-c3ccccc3)n(Cc3ccccc3)c2ncn1C[C@@H]1CCCC[C@H]1O] | 0.590 | 24.149 |
| 7 | 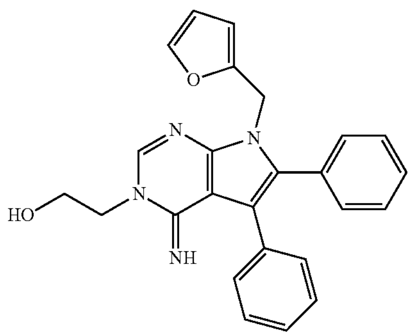 [SMILES: N=c1c2c(-c3ccccc3)c(-c3ccccc3)n(Cc3ccco3)c2ncn1CCO] | 0.628 | 20.434 |
| 74 | 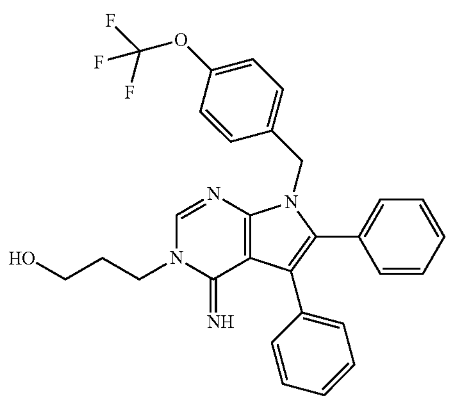 [SMILES: N=c1c2c(-c3ccccc3)c(-c3ccccc3)n(Cc3ccc(OC(F)(F)F)cc3)c2ncn1CCCO] | 0.743 | 24.149 |
| 19 | 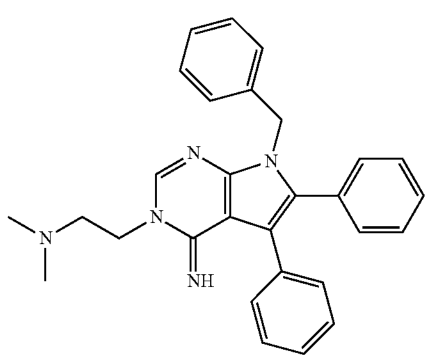 [SMILES: CN(C)CCn1cnc2c(c(-c3ccccc3)c(-c3ccccc3)n2Cc2ccccc2)c1=N] | 0.935 | 24.149 |

TABLE 4-continued
| Compound | Structure | PNC IC$_{50}$ (μM) | ATP IC$_{50}$ (μM) |
|---|---|---|---|
| 38 | 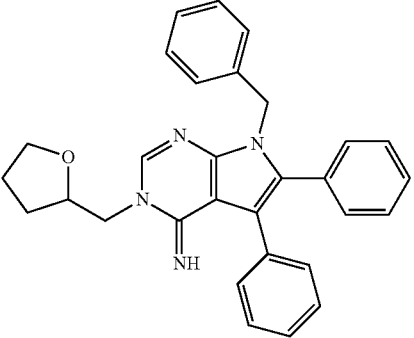 [SMILES: N=c1c2c(-c3ccccc3)c(-c3ccccc3)n(Cc3ccccc3)c2ncn1CC1CCCO1] | 0.935 | 96.138 |
| 76 | 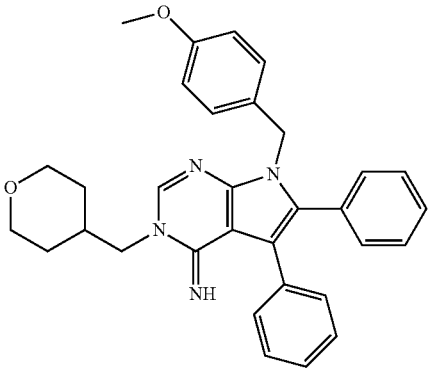 [SMILES: COc1ccc(Cn2c(-c3ccccc3)c(-c3ccccc3)c3c(=N)n(CC4CCOCC4)cnc32)cc1] | 0.935 | 48.183 |
| 75 | 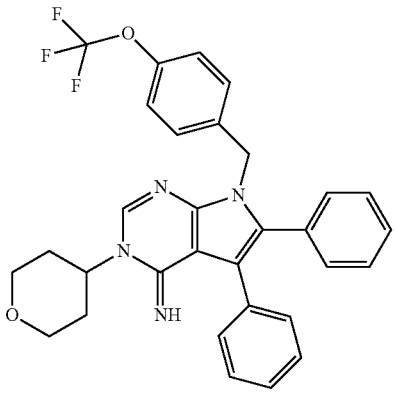 [SMILES: N=c1c2c(-c3ccccc3)c(-c3ccccc3)n(Cc3ccc(OC(F)(F)F)cc3)c2ncn1C1CCOCC1] | 0.935 | 24.149 |
| 14 | 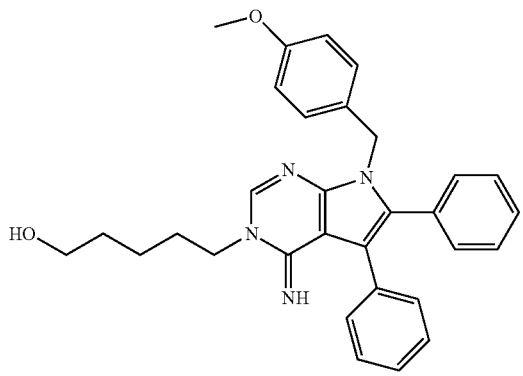 [SMILES: COc1ccc(Cn2c(-c3ccccc3)c(-c3ccccc3)c3c(=N)n(CCCCCO)cnc32)cc1] | 1.177 | 24.149 |

TABLE 4-continued

| Compound | Structure | PNC IC$_{50}$ (μM) | ATP IC$_{50}$(μM) |
|---|---|---|---|
| 27 | 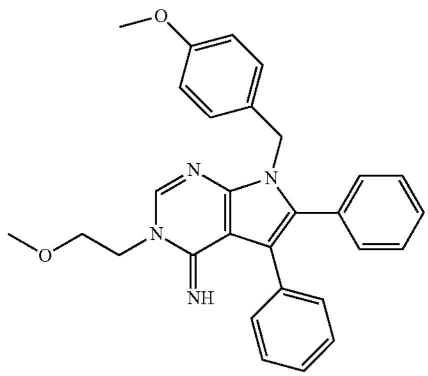 [SMILES: COCCn1cnc2c(c(-c3ccccc3)c(-c3ccccc3)n2Cc2ccc(OC)cc2)c1=N] | 1.177 | 24.149 |
| 17 | 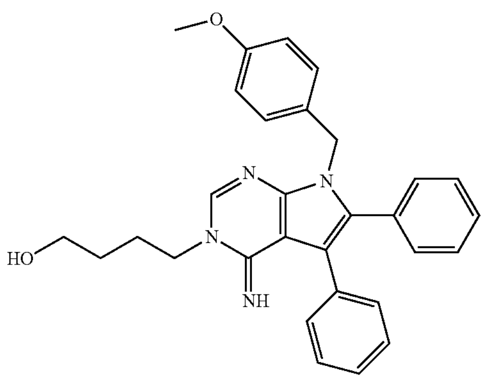 [SMILES: COc1ccc(Cn2c(-c3ccccc3)c(-c3ccccc3)c3c(=N)n(CCCCO)cnc32)cc1] | 1.177 | 30.402 |
| 77 | 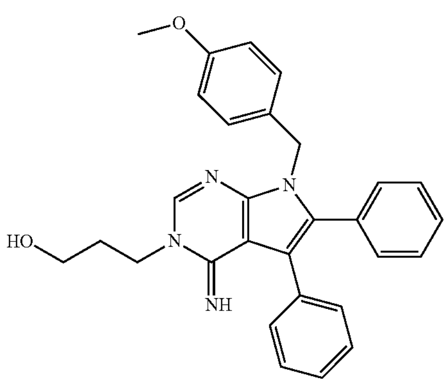 [SMILES: COc1ccc(Cn2c(-c3ccccc3)c(-c3ccccc3)c3c(=N)n(CCCO)cnc32)cc1] | 1.177 | 96.138 |
| 8 | 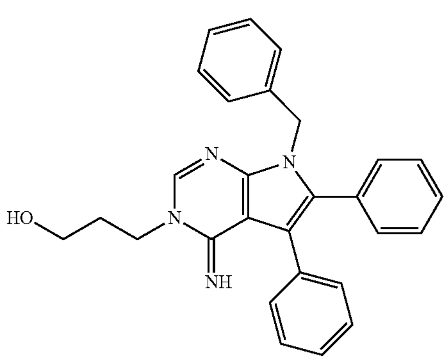 [SMILES: N=c1c2c(-c3ccccc3)c(-c3ccccc3)n(Cc3ccccc3)c2ncn1CCCO] | 1.254 | 20.434 |

TABLE 4-continued

| Compound | Structure | PNC IC$_{50}$ (μM) | ATP IC$_{50}$(μM) |
|---|---|---|---|
| 37 | 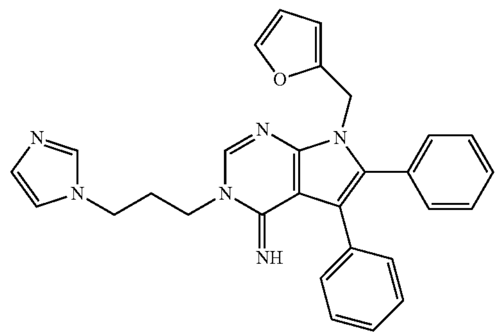 [SMILES: N=c1c2c(-c3ccccc3)c(-c3ccccc3)n(Cc3ccco3)c2ncn1CCCn1ccnc1] | 1.254 | 25.725 |
| 34 | 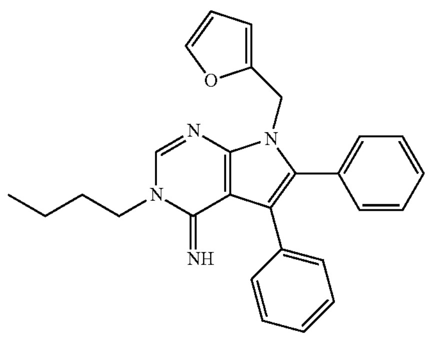 [SMILES: CCCCn1cnc2c(c(-c3ccccc3)c(-c3ccccc3)n2Cc2ccco2)c1=N] | 1.254 | 20.434 |
| 6 | 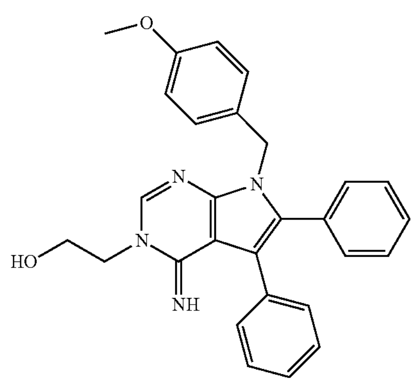 [SMILES: COc1ccc(Cn2c(-c3ccccc3)c(-c3ccccc3)c3c(=N)n(CCO)cnc32)cc1] | 1.482 | 48.183 |
| 78 | 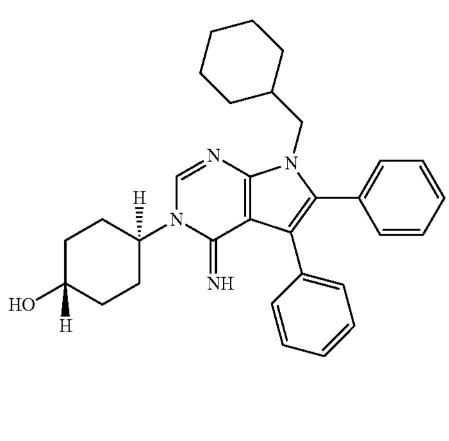 [SMILES: N=c1c2c(-c3ccccc3)c(-c3ccccc3)n(CC3CCCCC3)c2ncn1[C@H]1CC[C@H](O)CC1] | 1.482 | 30.402 |

TABLE 4-continued

| Compound | Structure | PNC IC$_{50}$ (μM) | ATP IC$_{50}$(μM) |
|---|---|---|---|
| 25 | 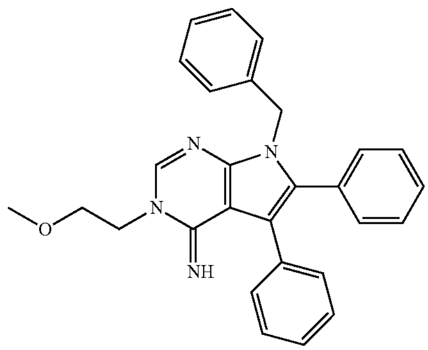 [SMILES: COCCn1cnc2c(c(-c3ccccc3)c(-c3ccccc3)n2Cc2ccccc2)c1=N] | 1.866 | 60.659 |
| 24 | 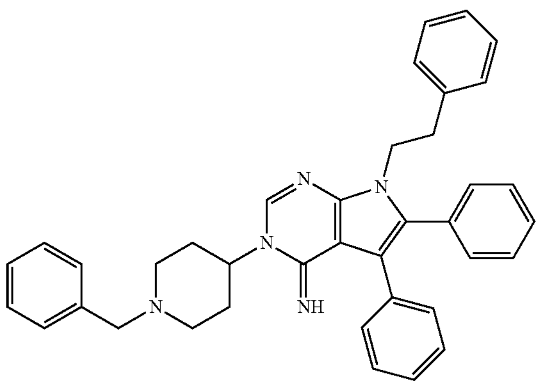 [SMILES: N=c1c2c(-c3ccccc3)c(-c3ccccc3)n(CCc3ccccc3)c2ncn1C1CCN(Cc2ccccc2)CC1] | 1.866 | 24.149 |
| 81 | 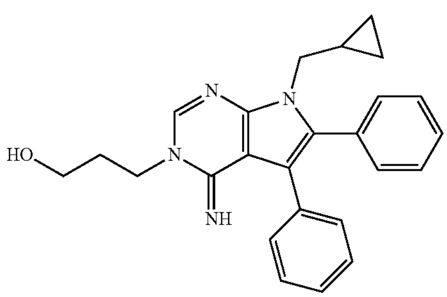 [SMILES: N=c1c2c(-c3ccccc3)c(-c3ccccc3)n(CC3CC3)c2ncn1CCCO] | 1.866 | 76.365 |
| 80 | 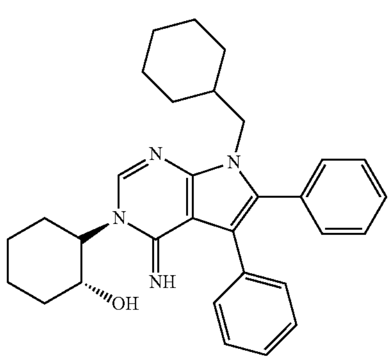 | 1.866 | 21.523 |

TABLE 4-continued
| Compound | Structure | PNC IC$_{50}$ (μM) | ATP IC$_{50}$(μM) |
|---|---|---|---|
| 79 | 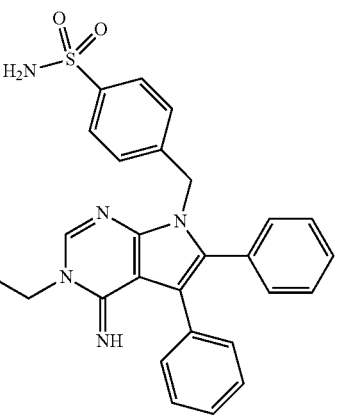 | 1.866 | 382.734 |
| 36 | 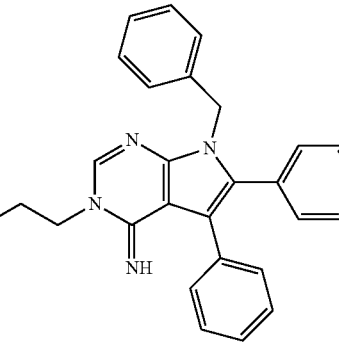 | 1.987 | 25.725 |
| 82 | 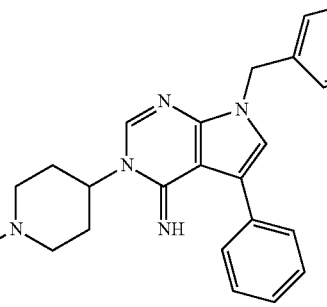 | 2.349 | 30.402 |
| 31 | 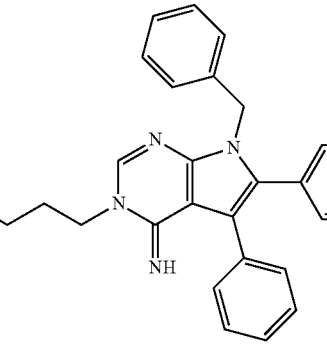 | 2.957 | 24.149 |

TABLE 4-continued

| Compound | Structure | PNC IC$_{50}$ (μM) | ATP IC$_{50}$(μM) |
|---|---|---|---|
| 83 | 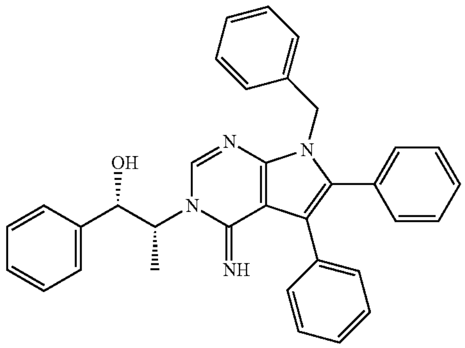 [SMILES: C[C@H]([C@@H](O)c1ccccc1)n1cnc2c(c(-c3ccccc3)c(-c3ccccc3)n2Cc2ccccc2)c1=N] | 2.957 | 24.149 |
| 33 | 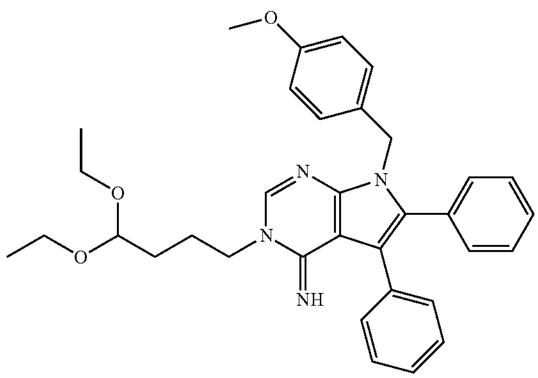 [SMILES: CCOC(CCCn1cnc2c(c(-c3ccccc3)c(-c3ccccc3)n2Cc2ccc(OC)cc2)c1=N)OCC] | 2.957 | 48.183 |
| 85 | 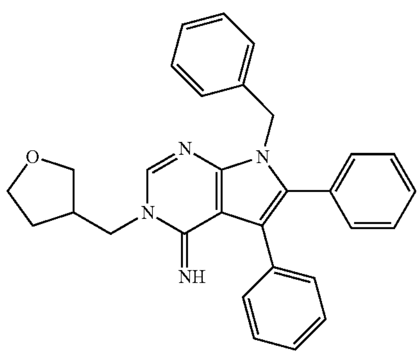 [SMILES: N=c1c2c(-c3ccccc3)c(-c3ccccc3)n(Cc3ccccc3)c2ncn1CC1CCOC1] | 2.957 | 24.149 |
| 84 | 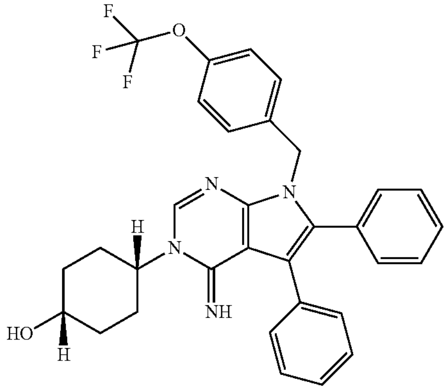 [SMILES: N=c1c2c(-c3ccccc3)c(-c3ccccc3)n(Cc3ccc(OC(F)(F)F)cc3)c2ncn1[C@H]1CC[C@@H](O)CC1] | 2.957 | 24.149 |

TABLE 4-continued

| Compound | Structure | PNC IC$_{50}$ (μM) | ATP IC$_{50}$(μM) |
|---|---|---|---|
| 26 | 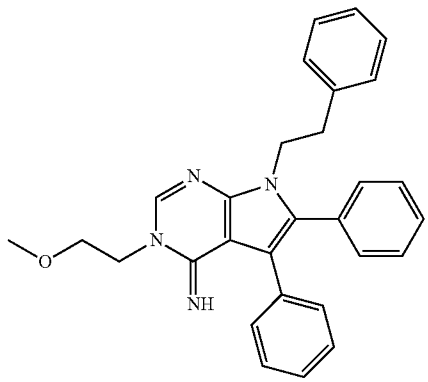 [SMILES: COCCn1cnc2c(c(-c3ccccc3)c(-c3ccccc3)n2CCc2ccccc2)c1=N] | 3.722 | 60.659 |
| 86 | 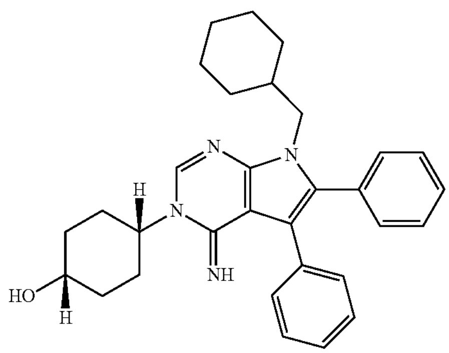 [SMILES: N=c1c2c(-c3ccccc3)c(-c3ccccc3)n(CC3CCCCC3)c2ncn1[C@H]1CC[C@@H](O)CC1] | 3.722 | 24.149 |
| 11 | 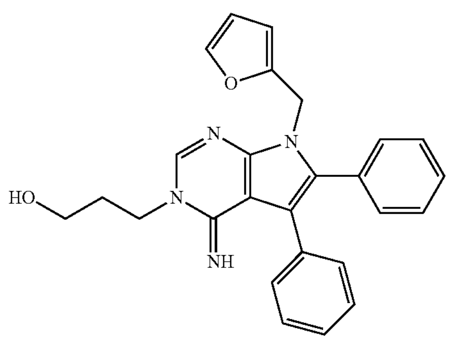 [SMILES: N=c1c2c(-c3ccccc3)c(-c3ccccc3)n(Cc3ccco3)c2ncn1CCCO] | 3.965 | 64.618 |
| 23 | 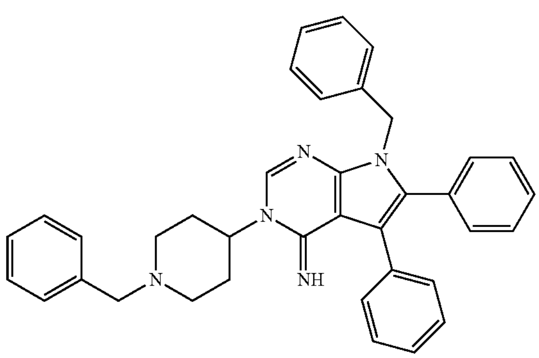 [SMILES: N=c1c2c(-c3ccccc3)c(-c3ccccc3)n(Cc3ccccc3)c2ncn1C1CCN(Cc2ccccc2)CC1] | 4.686 | 121.031 |

TABLE 4-continued

| Compound | Structure | PNC IC$_{50}$ (µM) | ATP IC$_{50}$(µM) |
|---|---|---|---|
| 39 | 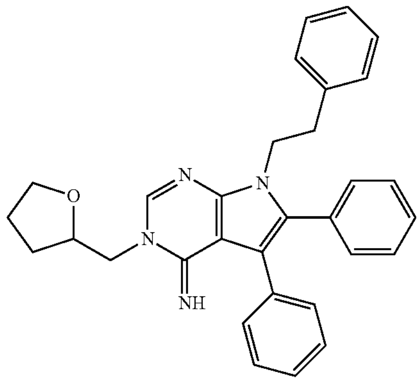 [SMILES: N=c1c2c(-c3ccccc3)c(-c3ccccc3)n(CCc3ccccc3)c2ncn1CC1CCCO1] | 4.686 | 48.183 |
| 48 | 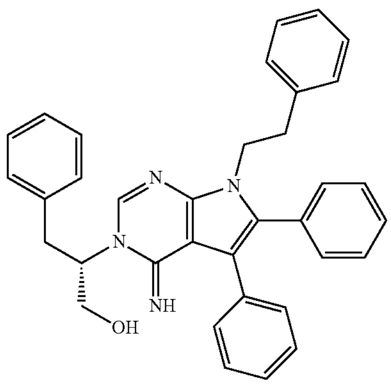 [SMILES: N=c1c2c(-c3ccccc3)c(-c3ccccc3)n(CCc3ccccc3)c2ncn1[C@H](CO)Cc1ccccc1] | 4.686 | 30.402 |
| 88 | 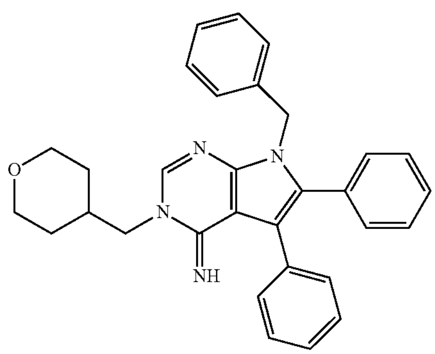 [SMILES: N=c1c2c(-c3ccccc3)c(-c3ccccc3)n(Cc3ccccc3)c2ncn1CC1CCOCC1] | 4.686 | 30.402 |
| 87 | 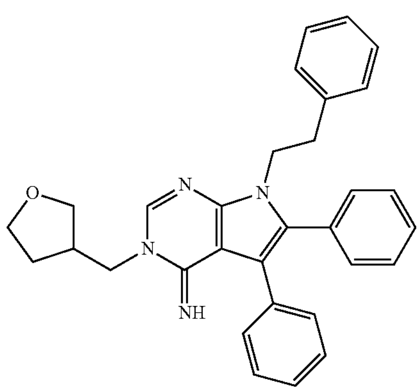 [SMILES: N=c1c2c(-c3ccccc3)c(-c3ccccc3)n(CCc3ccccc3)c2ncn1CC1CCOC1] | 4.686 | 60.659 |

TABLE 4-continued

| Compound | Structure | PNC IC$_{50}$ (μM) | ATP IC$_{50}$ (μM) |
|---|---|---|---|
|  |  | 5.899 | 38.273 |
| 30 | 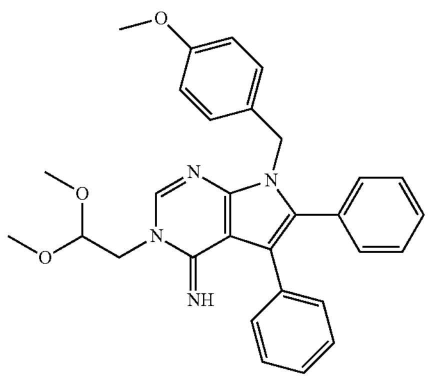 [SMILES: COc1ccc(Cn2c(-c3ccccc3)c(-c3ccccc3)c3c(=N)n(CC(OC)OC)cnc32)cc1] | 5.899 | 24.149 |
| 40 | 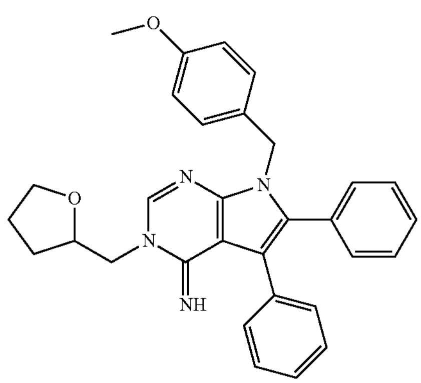 [SMILES: COc1ccc(Cn2c(-c3ccccc3)c(-c3ccccc3)c3c(=N)n(CC4CCCO4)cnc32)cc1] | 5.899 | 38.273 |
| 90 | 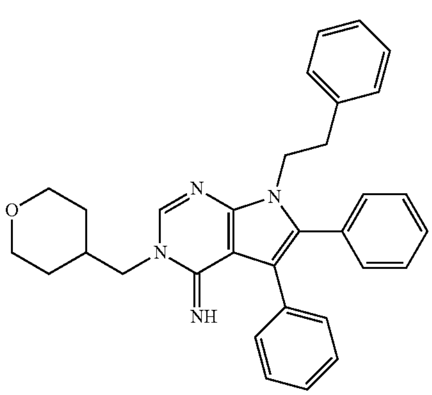 [SMILES: N=c1c2c(-c3ccccc3)c(-c3ccccc3)n(CCc3ccccc3)c2ncn1CC1CCOCC1] | 5.899 | 76.365 |

TABLE 4-continued

| Compound | Structure | PNC IC$_{50}$ (μM) | ATP IC$_{50}$(μM) |
|---|---|---|---|
| 89 | 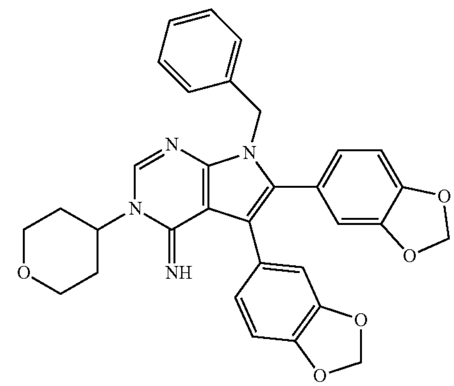 [SMILES: N=c1c2c(-c3ccc4c(c3)OCO4)c(-c3ccc4c(c3)OCO4)n(Cc3ccccc3)c2ncn1C1CCOCC1] | 5.899 | 24.149 |
| 91 | 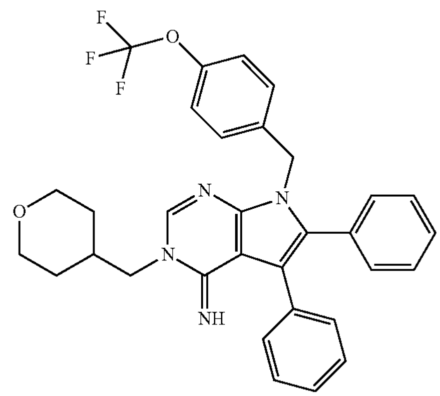 [SMILES: N=c1c2c(-c3ccccc3)c(-c3ccccc3)n(Cc3ccc(OC(F)(F)F)cc3)c2ncn1CC1CCOCC1] | 5.899 | 30.402 |
| 21 | 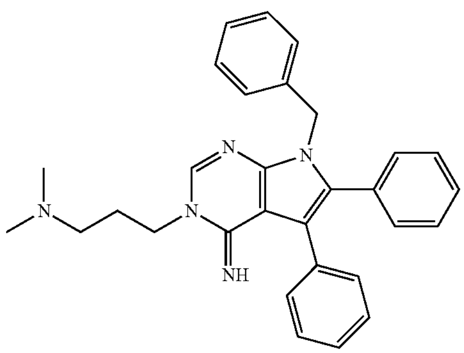 [SMILES: CN(C)CCCn1cnc2c(c(-c3ccccc3)c(-c3ccccc3)n2Cc2ccccc2)c1=N] | 7.427 | 24.149 |
| 22 | 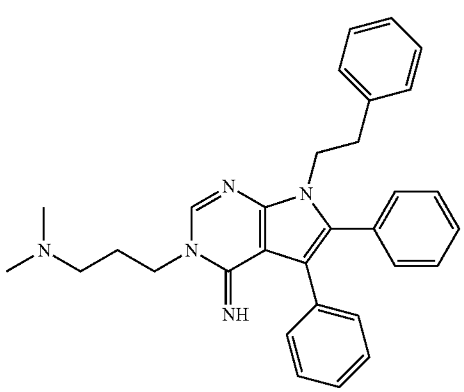 [SMILES: CN(C)CCCn1cnc2c(c(-c3ccccc3)c(-c3ccccc3)n2CCc2ccccc2)c1=N] | 7.427 | 24.149 |

TABLE 4-continued
| Compound | Structure | PNC IC$_{50}$ (μM) | ATP IC$_{50}$(μM) |
|---|---|---|---|
| 97 | 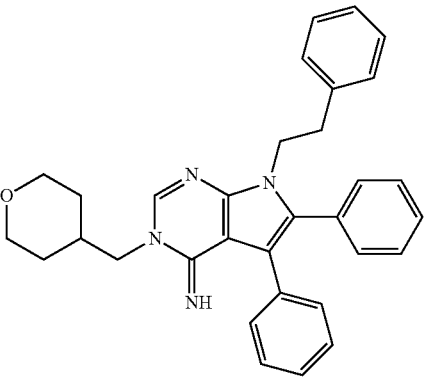 [SMILES: N=c1c2c(-c3ccccc3)c(-c3ccccc3)n(CCc3ccccc3)c2ncn1CC1CCOCC1] | 7.427 | 96.138 |
| 93 | 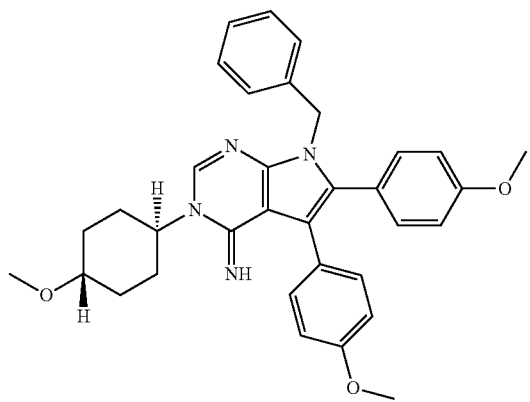 | 7.427 | 60.659 |
| 45 | 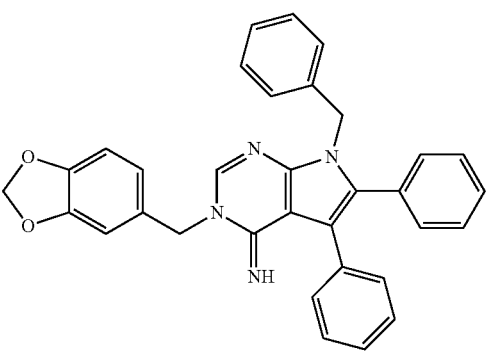 [SMILES: N=c1c2c(-c3ccccc3)c(-c3ccccc3)n(Cc3ccccc3)c2ncn1Cc1ccc2c(c1)OCO2] | 9.350 | 24.149 |
| 94 | 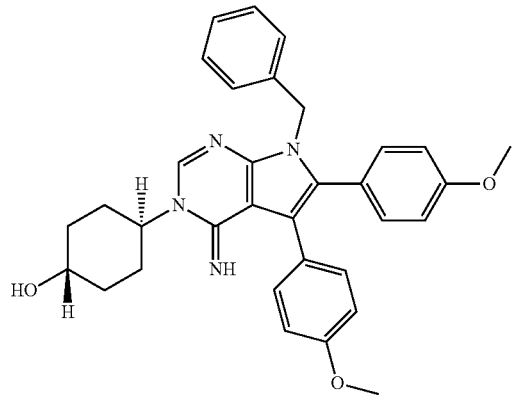 [SMILES: COc1ccc(-c2c(-c3ccc(OC)cc3)n(Cc3ccccc3)c3ncn([C@H]4CC[C@H](O)CC4)c(=N)c23)cc1] | 9.350 | 24.149 |

TABLE 4-continued
| Compound | Structure | PNC IC$_{50}$ (μM) | ATP IC$_{50}$(μM) |
|---|---|---|---|
| 43 | 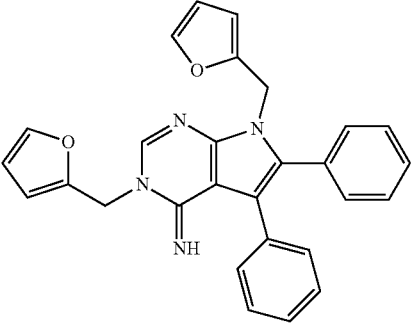 [SMILES: N=c1c2c(-c3ccccc3)c(-c3ccccc3)n(Cc3ccco3)c2ncn1Cc1ccco1] | 9.960 | 20.434 |
| 96 | 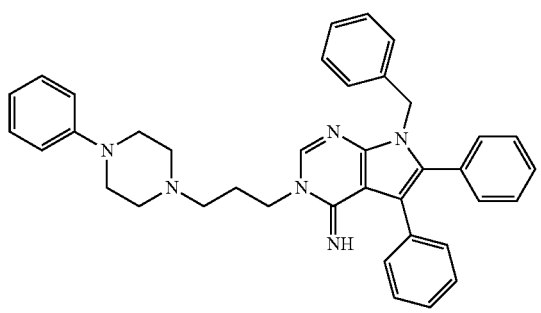 [SMILES: N=c1c2c(-c3ccccc3)c(-c3ccccc3)n(Cc3ccccc3)c2ncn1CCCN1CCN(c2ccccc2)CC1] | 11.770 | 30.402 |
| 95 | 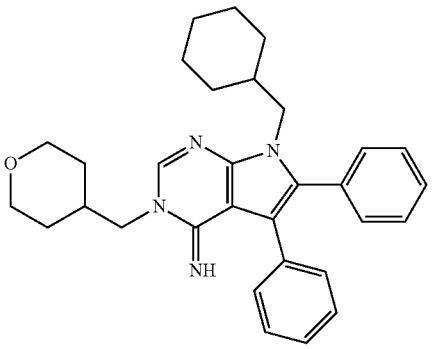 [SMILES: N=c1c2c(-c3ccccc3)c(-c3ccccc3)n(CC3CCCCC3)c2ncn1CC1CCOCC1] | 11.770 | 24.149 |
| 99 | 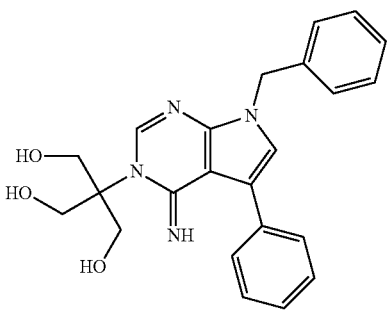 [SMILES: N=c1c2c(-c3ccccc3)cn(Cc3ccccc3)c2ncn1C(CO)(CO)CO] | 14.818 | inactive |

TABLE 4-continued

| Compound | Structure | PNC IC$_{50}$ (μM) | ATP IC$_{50}$(μM) |
|---|---|---|---|
| 46 | 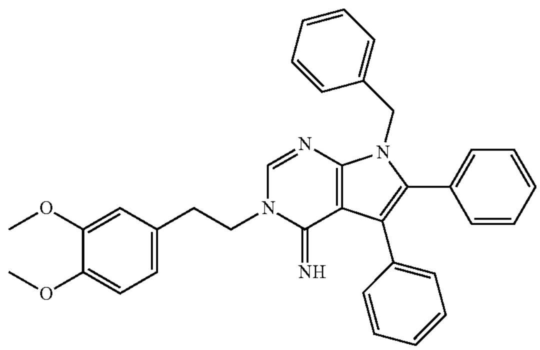 [SMILES: COc1ccc(CCn2cnc3c(c(-c4ccccc4)c(-c4ccccc4)n3Cc3ccccc3)c2=N)cc1OC] | 14.818 | 24.149 |
| 98 | 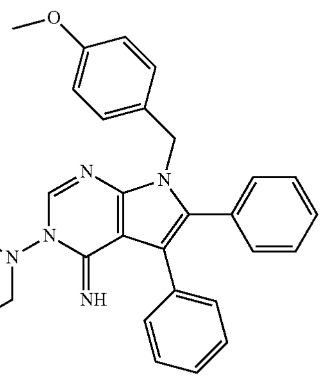 | 14.818 | 121.031 |
| 101 | 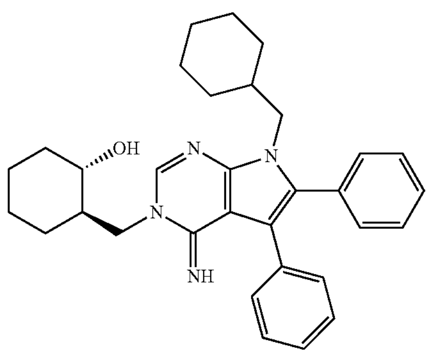 [SMILES: N=c1c2c(-c3ccccc3)c(-c3ccccc3)n(CC3CCCCC3)c2ncn1C[C@H]1CCCC[C@@H]1O] | 14.818 | 24.149 |
| 97 | 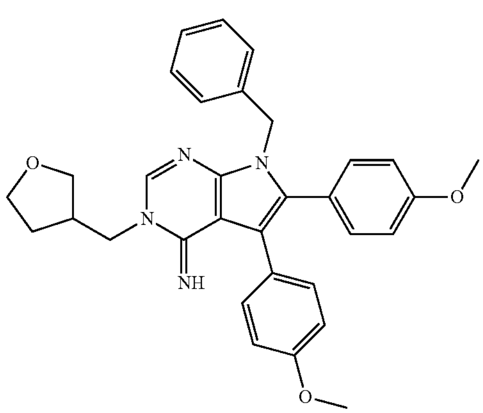 [SMILES: COc1ccc(-c2c(-c3ccc(OC)cc3)n(Cc3ccccc3)c3ncn(CC4CCOC4)c(=N)c23)cc1] | 14.818 | 48.183 |

TABLE 4-continued

| Compound | Structure | PNC IC$_{50}$ (μM) | ATP IC$_{50}$(μM) |
|---|---|---|---|
| 100 | 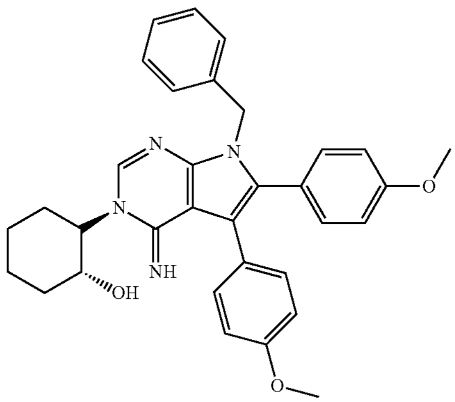 | 14.818 | 48.183 |
| 102 | 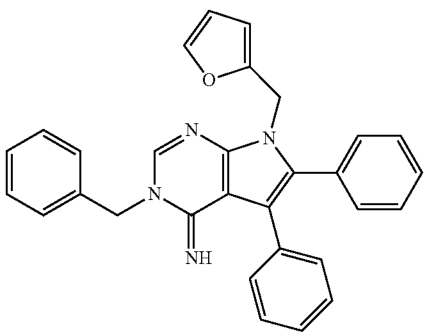 [SMILES: N=c1c2c(-c3ccccc3)c(-c3ccccc3)n(Cc3ccco3)c2ncn1Cc1ccccc1] | 15.785 | 25.725 |
| 141 | 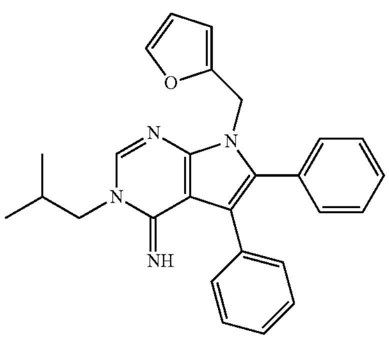 [SMILES: CC(C)Cn1cnc2c(c(-c3ccccc3)c(-c3ccccc3)n2Cc2ccco2)c1=N] | 15.785 | 20.434 |
| 32 | 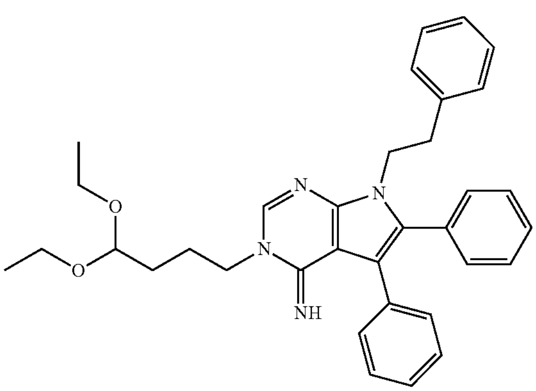 [SMILES: CCOC(CCCn1cnc2c(c(-c3ccccc3)c(-c3ccccc3)n2CCc2ccccc2)c1=N)OCC] | 18.655 | 24.149 |

TABLE 4-continued
| Compound | Structure | PNC IC$_{50}$ (μM) | ATP IC$_{50}$(μM) |
|---|---|---|---|
| 103 | 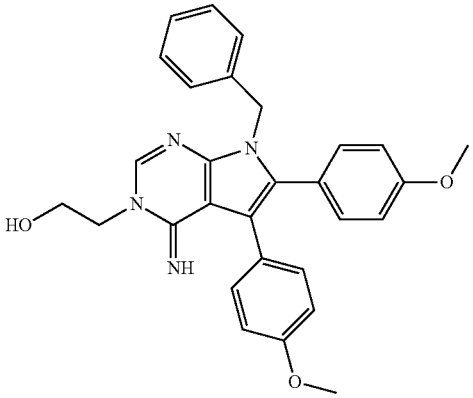 [SMILES: COc1ccc(-c2c(-c3ccc(OC)cc3)n(Cc3ccccc3)c3ncn(CCO)c(=N)c23)cc1] | 18.655 | 24.149 |
| 29 | 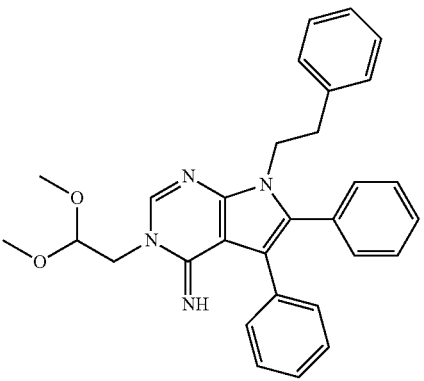 [SMILES: COC(Cn1cnc2c(c(-c3ccccc3)c(-c3ccccc3)n2CCc2ccccc2)c1=N)OC] | 23.485 | 27.096 |
| 104 | 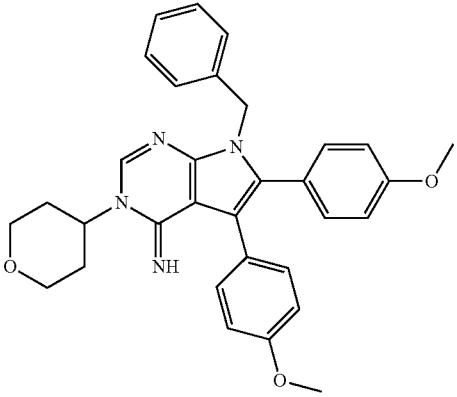 [SMILES: COc1ccc(-c2c(-c3ccc(OC)cc3)n(Cc3ccccc3)c3ncn(C4CCOCC4)c(=N)c23)cc1] | 23.485 | 30.402 |
| 106 | 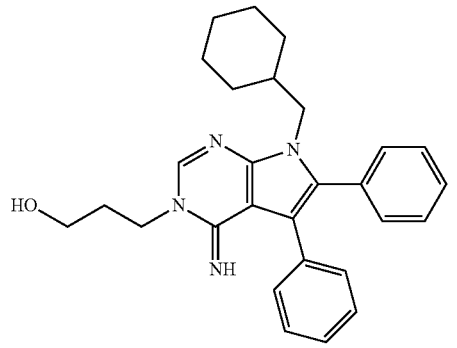 [SMILES: N=c1c2c(-c3ccccc3)c(-c3ccccc3)n(CC3CCCCC3)c2ncn1CCCO] | 23.485 | 30.402 |

TABLE 4-continued
| Compound | Structure | PNC IC$_{50}$ (µM) | ATP IC$_{50}$ (µM) |
|---|---|---|---|
| 105 | 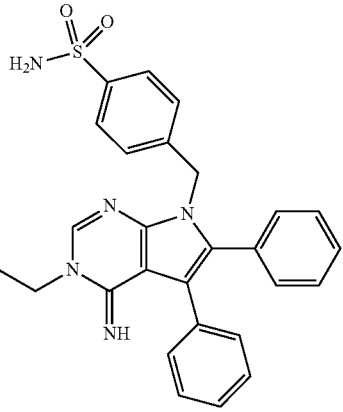 | 23.485 | 304.016 |
| 107 | 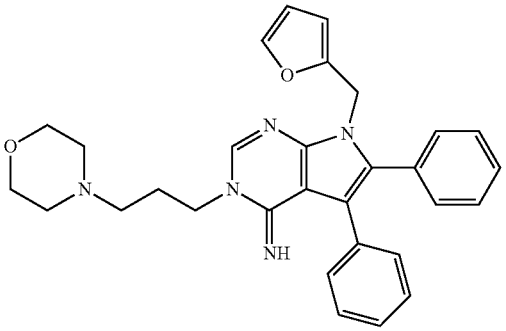 [SMILES: N=c1c2c(-c3ccccc3)c(-c3ccccc3)n(Cc3ccco3)c2ncn1CCCN1CCOCC1] | 25.018 | 32.386 |
| 108 | 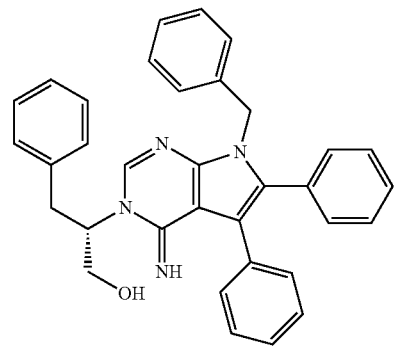 [SMILES: N=c1c2c(-c3ccccc3)c(-c3ccccc3)n(Cc3ccccc3)c2ncn1[C@H](CO)Cc1ccccc1] | 29.566 | 38.273 |
| 53 | 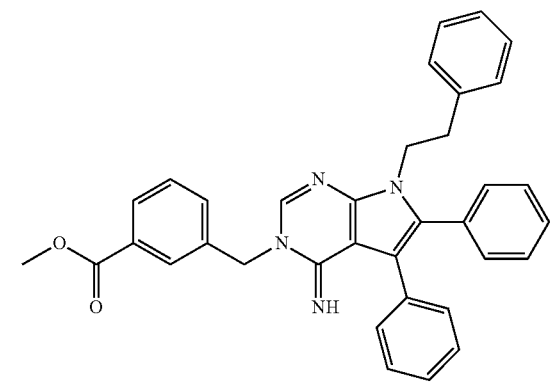 [SMILES: COC(=O)c1cccc(Cn2cnc3c(c(-c4ccccc4)c(-c4ccccc4)n3CCc3ccccc3)c2=N)c1] | 29.566 | 24.149 |

TABLE 4-continued

| Compound | Structure | PNC IC$_{50}$ (μM) | ATP IC$_{50}$(μM) |
|---|---|---|---|
| 37 | 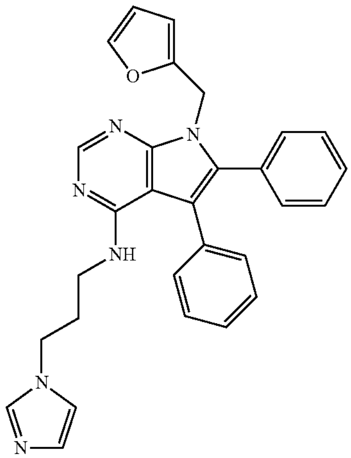 [SMILES: c1ccc(-c2c(-c3ccccc3)n(Cc3ccco3)c3ncnc(NCCCn4ccnc4)c23)cc1] | 39.650 | 81.349 |
| 110 | 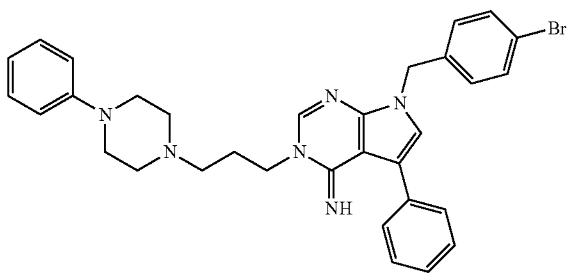 [SMILES: N=c1c2c(-c3ccccc3)cn(Cc3ccc(Br)cc3)c2ncn1CCCN1CCN(c2ccccc2)CC1] | 46.859 | 30.402 |
| 109 | 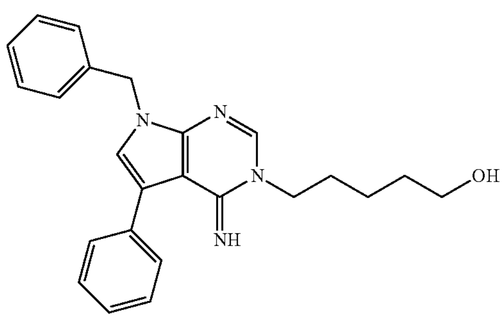 [SMILES: N=c1c2c(-c3ccccc3)cn(Cc3ccccc3)c2ncn1CCCCCO] | 46.859 | 96.138 |
| 111 | 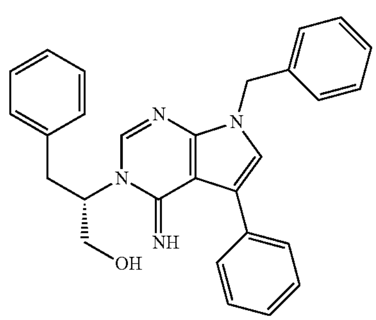 [SMILES: N=c1c2c(-c3ccccc3)cn(Cc3ccccc3)c2ncn1[C@H](CO)Cc1ccccc1] | 93.496 | 121.031 |

TABLE 4-continued
| Compound | Structure | PNC IC$_{50}$ (μM) | ATP IC$_{50}$ (μM) |
|---|---|---|---|
| 137 | 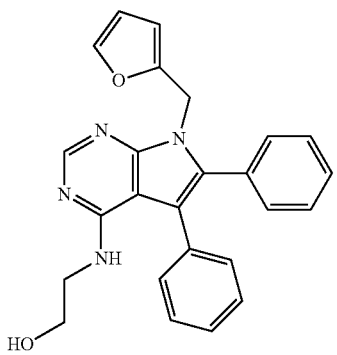 [SMILES: OCCNc1ncnc2c1c(-c1ccccc1)c(-c1ccccc1)n2Cc1ccco1] | inactive | inactive |
| 50 | 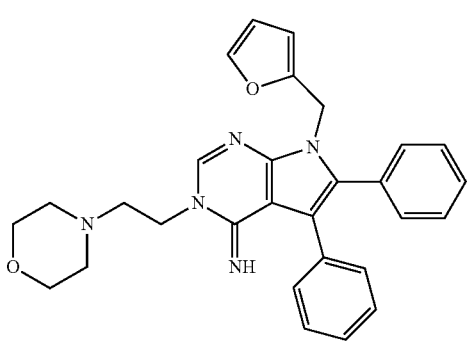 [SMILES: N=c1c2c(-c3ccccc3)c(-c3ccccc3)n(Cc3ccco3)c2ncn1CCN1CCOCC1] | inactive | 32.386 |
| 116 | 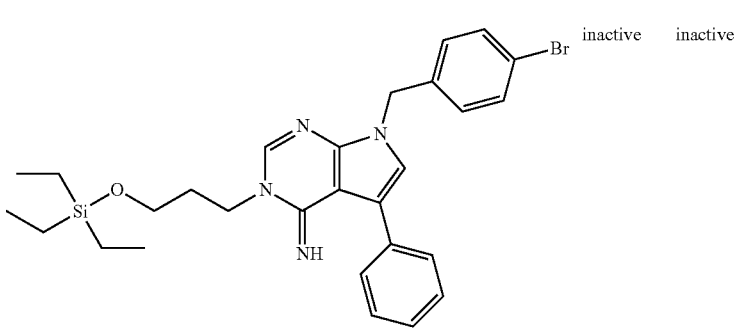 | inactive | inactive |
| 10 | 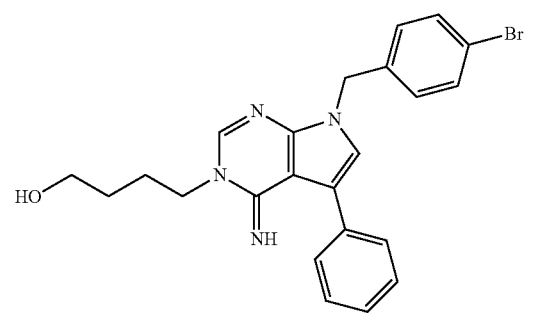 [SMILES: N=c1c2c(-c3ccccc3)cn(Cc3ccc(Br)cc3)c2ncn1CCCCO] | inactive | 96.138 |

TABLE 4-continued

| Compound | Structure | PNC IC$_{50}$ (µM) | ATP IC$_{50}$(µM) |
|---|---|---|---|
| 114 | 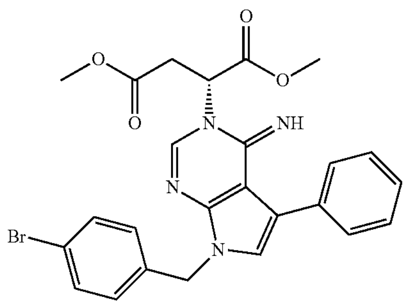 [SMILES: COC(=O)C[C@H](C(=O)OC)n1cnc2c(c(-c3ccccc3)cn2Cc2ccc(Br)cc2)c1=N] | inactive | inactive |
| 140 | 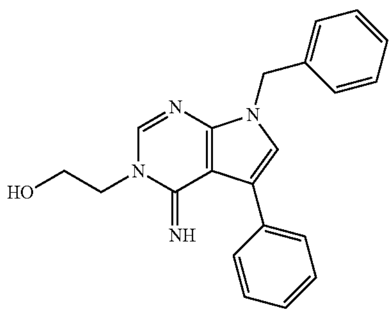 [SMILES: N=c1c2c(-c3ccccc3)cn(Cc3ccccc3)c2ncn1CCO] | inactive | inactive |
| 118 | 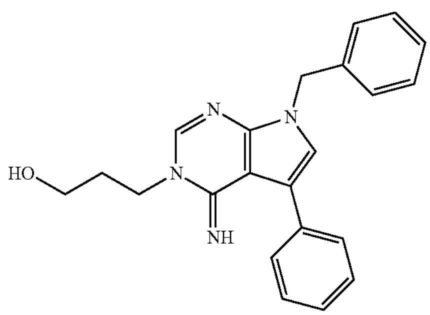 [SMILES: N=c1c2c(-c3ccccc3)cn(Cc3ccccc3)c2ncn1CCCO] | inactive | 121.031 |
| 125 | 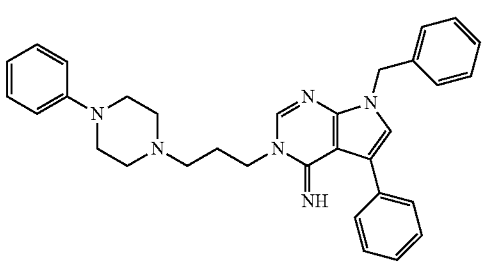 [SMILES: N=c1c2c(-c3ccccc3)cn(Cc3ccccc3)c2ncn1CCCN1CCN(c2ccccc2)CC1] | inactive | 30.402 |
| 10 | 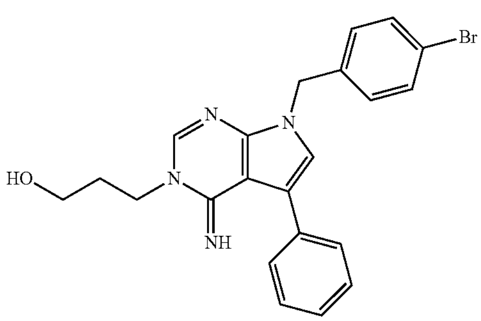 [SMILES: N=c1c2c(-c3ccccc3)cn(Cc3ccc(Br)cc3)c2ncn1CCCO] | inactive | 48.183 |

TABLE 4-continued
| Compound | Structure | PNC IC$_{50}$ (μM) | ATP IC$_{50}$(μM) |
|---|---|---|---|
| 120 | 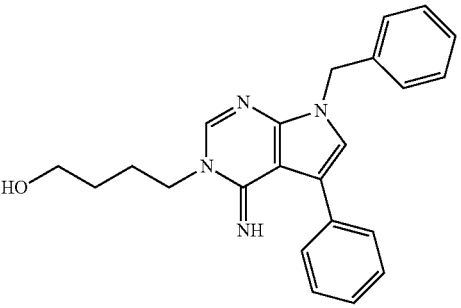 [SMILES: N=c1c2c(-c3ccccc3)cn(Cc3ccccc3)c2ncn1CCCCO] | inactive | 241.489 |
| 139 | 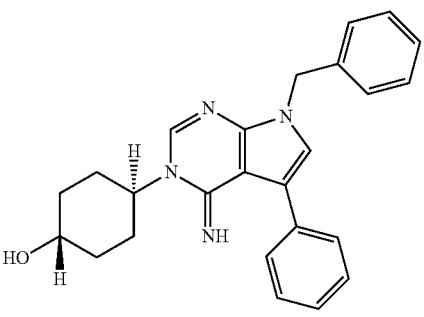 [SMILES: N=c1c2c(-c3ccccc3)cn(Cc3ccccc3)c2ncn1[C@H]1CC[C@H](O)CC1] | inactive | inactive |
| 128 | 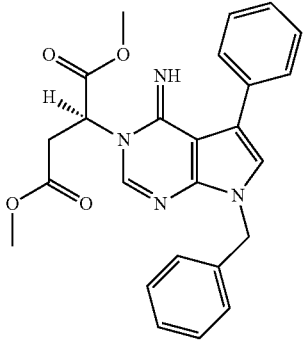 [SMILES: COC(=O)C[C@@H](C(=O)OC)n1cnc2c(c(-c3ccccc3)cn2Cc2ccccc2)c1=N] | inactive | inactive |
| 130 | 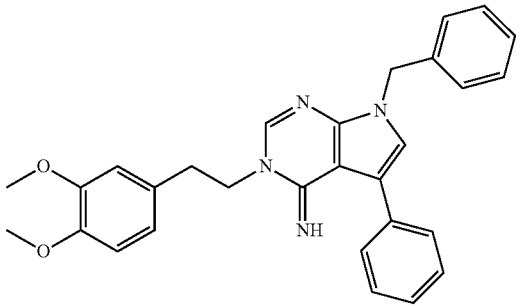 [SMILES: COc1ccc(CCn2cnc3c(c(-c4ccccc4)cn3Cc3ccccc3)c2=N)cc1OC] | inactive | 24.149 |

TABLE 4-continued

| Compound | Structure | PNC IC$_{50}$ (μM) | ATP IC$_{50}$(μM) |
|---|---|---|---|
| 136 | 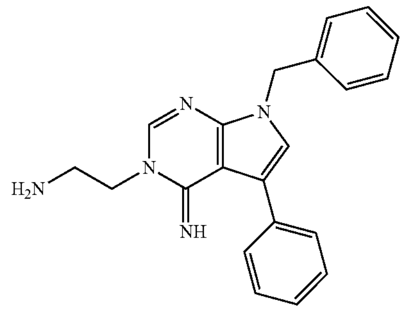 [SMILES: N=c1c2c(-c3ccccc3)cn(Cc3ccccc3)c2ncn1CCN] | inactive | inactive |
| 131 | 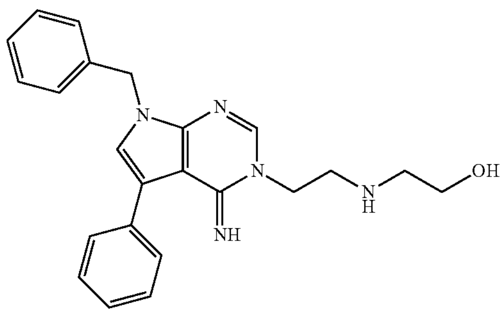 [SMILES: N=c1c2c(-c3ccccc3)cn(Cc3ccccc3)c2ncn1CCNCCO] | inactive | 121.031 |
| 119 | 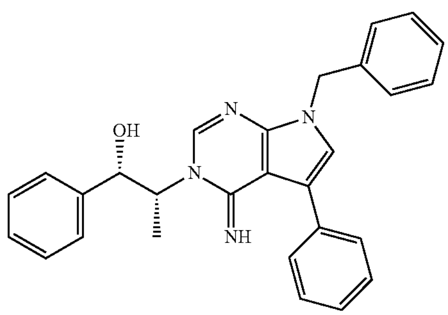 [SMILES: C[C@H]([C@@H](O)c1ccccc1)n1cnc2c(c(-c3ccccc3)cn2Cc2ccccc2)c1=N] | inactive | 121.031 |
| 117 | 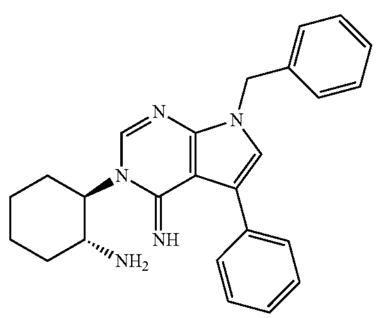 [SMILES: N=c1c2c(-c3ccccc3)cn(Cc3ccccc3)c2ncn1[C@@H]1CCCC[C@H]1N] | inactive | 96.138 |
| 122 | 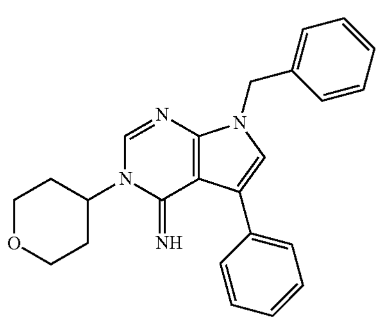 [SMILES: N=c1c2c(-c3ccccc3)cn(Cc3ccccc3)c2ncn1C1CCOCC1] | inactive | inactive |

TABLE 4-continued
| Compound | Structure | PNC IC$_{50}$ (μM) | ATP IC$_{50}$(μM) |
|---|---|---|---|
| 115 | 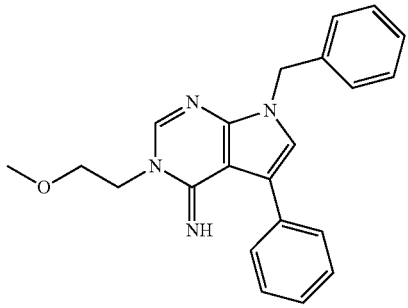 [SMILES: COCCn1cnc2c(c(-c3ccccc3)cn2Cc2ccccc2)c1=N] | inactive | 121.031 |
| 127 | 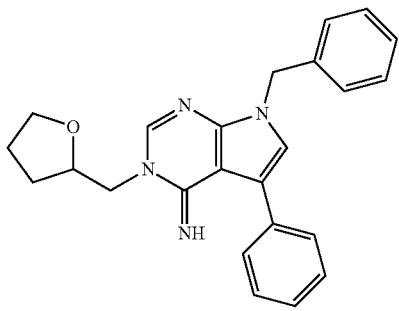 [SMILES: N=c1c2c(-c3ccccc3)cn(Cc3ccccc3)c2ncn1CC1CCCO1] | inactive | 96.138 |
| 124 | 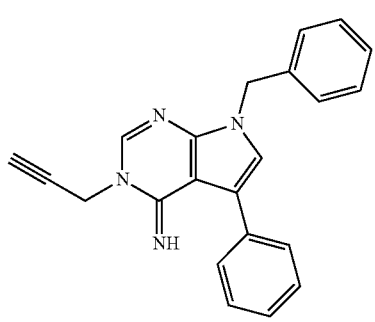 [SMILES: C#CCn1cnc2c(c(-c3ccccc3)cn2Cc2ccccc2)c1=N] | inactive | inactive |
| 138 | 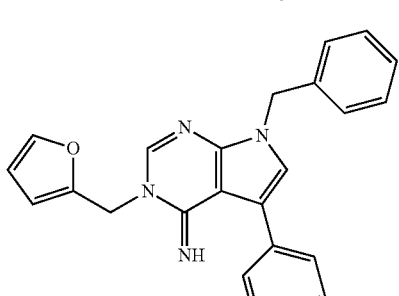 | inactive | 60.659 |
| 121 | 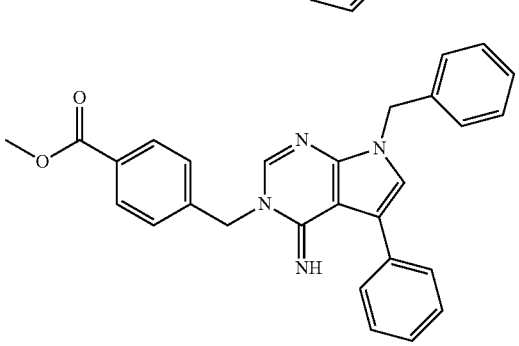 | inactive | 121.031 |

TABLE 4-continued

| Compound | Structure | PNC IC$_{50}$ (μM) | ATP IC$_{50}$(μM) |
|---|---|---|---|
| 12 | 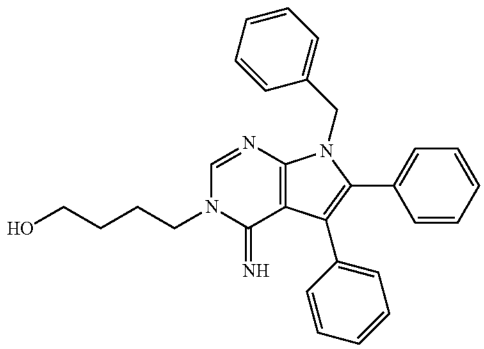 [SMILES: N=c1c2c(-c3ccccc3)c(-c3ccccc3)n(Cc3ccccc3)c2ncn1CCCCO] | inactive | 24.149 |
| 18 | 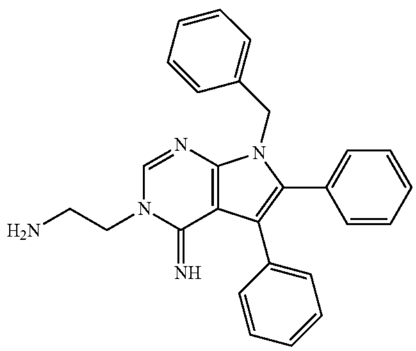 [SMILES: N=c1c2c(-c3ccccc3)c(-c3ccccc3)n(Cc3ccccc3)c2ncn1CCN] | inactive | 76.365 |
| 112 | 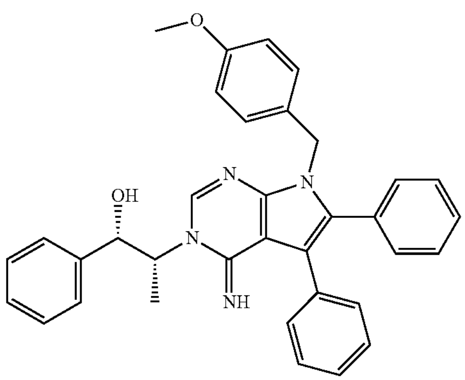 [SMILES: COc1ccc(Cn2c(-c3ccccc3)c(-c3ccccc3)c3c(=N)n([C@H](C)[C@@H](O)c4ccccc4)cnc32)cc1] | inactive | 60.659 |
| 132 | 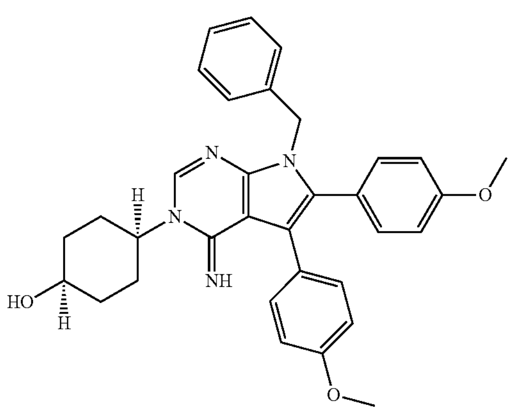 [SMILES: COc1ccc(-c2c(-c3ccc(OC)cc3)n(Cc3ccccc3)c3ncn([C@H]4CC[C@@H](O)CC4)c(=N)c23)cc1] | inactive | inactive |

TABLE 4-continued

| Compound | Structure | PNC IC$_{50}$ (μM) | ATP IC$_{50}$ (μM) |
|---|---|---|---|
| 126 | 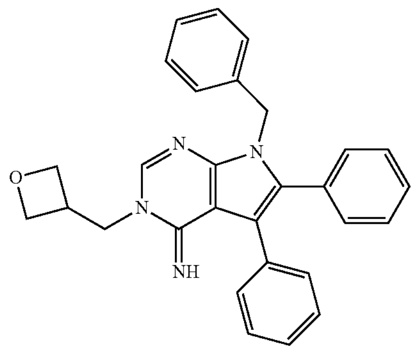 [SMILES: N=c1c2c(-c3ccccc3)c(-c3ccccc3)n(Cc3ccccc3)c2ncn1CC1COC1] | inactive | 96.138 |
| 129 | 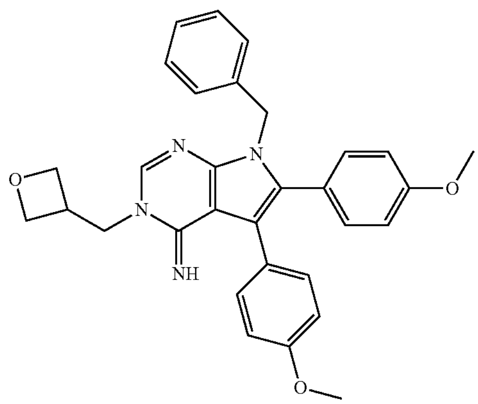 [SMILES: COc1ccc(-c2c(-c3ccc(OC)cc3)n(Cc3ccccc3)c3ncn(CC4COC4)c(=N)c23)cc1] | inactive | inactive |
| 135 | 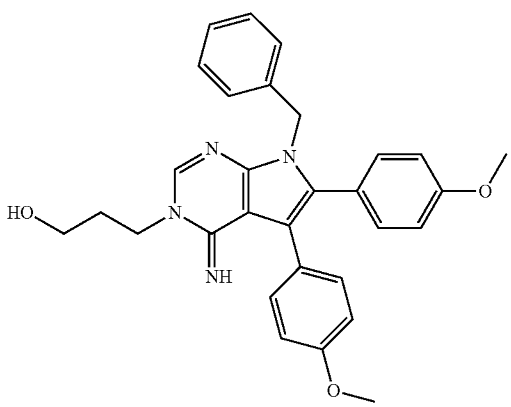 [SMILES: COc1ccc(-c2c(-c3ccc(OC)cc3)n(Cc3ccccc3)c3ncn(CCCO)c(=N)c23)cc1] | inactive | 30.402 |
| 134 | 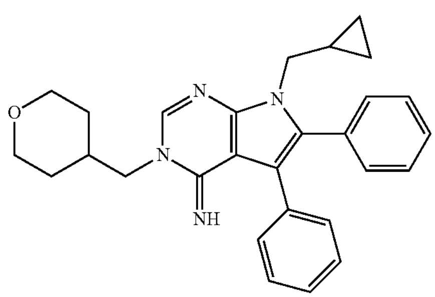 [SMILES: N=c1c2c(-c3ccccc3)c(-c3ccccc3)n(CC3CC3)c2ncn1CC1CCOCC1] | inactive | 60.659 |

TABLE 4-continued

| Compound | Structure | PNC IC$_{50}$ (μM) | ATP IC$_{50}$ (μM) |
|---|---|---|---|
| 123 | 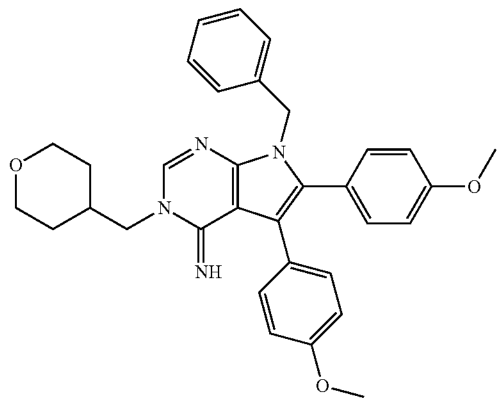 [SMILES: COc1ccc(-c2c(-c3ccc(OC)cc3)n(Cc3ccccc3)c3ncn(CC4CCOCC4)c(=N)c23)cc1] | inactive | 24.149 |
| 113 | 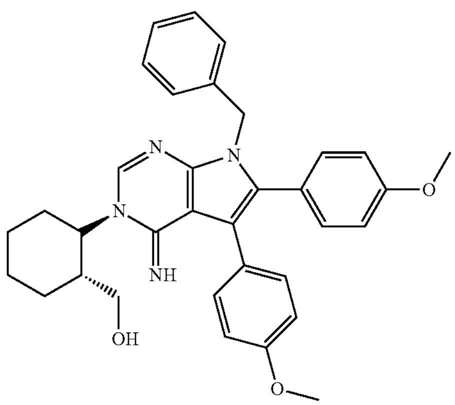 | inactive | 30.402 |
| 35 | 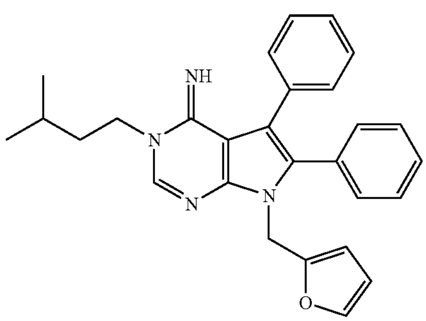 [SMILES: CC(C)CCn1cnc2c(c(-c3ccccc3)c(-c3ccccc3)n2Cc2ccco2)c1=N] | Inactive | 19.87 |
| 44 | 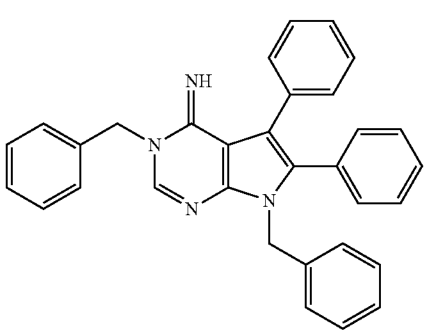 [SMILES: N=c1c2c(-c3ccccc3)c(-c3ccccc3)n(Cc3ccccc3)c2ncn1Cc1ccccc1] | 15.79 | 19.87 |

All references, including publications, patent applications, and patents, cited herein are hereby incorporated by reference to the same extent as if each reference were individually and specifically indicated to be incorporated by reference and were set forth in its entirety herein.

The terms "comprising," "having," "including," and "containing" are to be construed as open-ended terms (that is meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (such as, "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula (I):

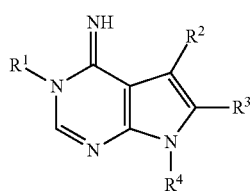

wherein $R^1$ is selected from the group consisting thioalkyl, alkoxyalkyl, alkylthioalkyl, cycloalkyl, hydroxycycloalkyl, hydroxycycloalkylalkyl, thiocycloalkyl, alkoxycycloalkyl, alkylthiocycloalkyl, dialkylaminoalkyl, heterocyclyl, heteroaryl, arylalkylpiperidin-4-yl, arylpiperazinylalkyl, (tetrahydrofuran-3-yl)methyl, and (tetrahydrofuran-2-yl)methyl and (tetrahydro-2H-pyran-4-yl)methyl, $R^2$ is phenyl, optionally substituted with one or more substituents selected from the group consisting of halo, alkyl, hydroxyalkyl, thioalkyl, alkoxy, alkylthioalkyl, alkoxycarbonyl, alkylthiocarbonyl, amino, alkylamino, dialkylamino, and alkylcarbonyl, $R^3$ is phenyl, optionally substituted with one or more substituents selected from the group consisting of halo, alkyl, hydroxyalkyl, thioalkyl, alkoxy, alkylthioalkyl, alkoxycarbonyl, alkylthiocarbonyl, amino, alkylamino, dialkylamino, and alkylcarbonyl, $R^4$ is selected from the group consisting of alkyl, cycloalkyl, cycloalkylalkyl, aryl, heteroaryl, and arylalkyl, or a pharmaceutically acceptable salt thereof, wherein $R^4$ is optionally substituted on the aryl and/or alkyl portion with one or more substituents selected from the group consisting of halo, alkyl, hydroxyalkyl, thioalkyl, alkylthioalkyl, alkoxycarbonyl, alkylthiocarbonyl, amino, alkylamino, dialkylamino, aminosulfonyl, hydroxyl, perfluoroalkoxy, alkylenedioxy, and alkylcarbonyl.

2. The compound or salt of claim 1, wherein $R^4$ is benzyl, wherein the phenyl ring is optionally substituted with one or more substituents selected from the group consisting of alkyl, hydroxyalkyl, thioalkyl, alkylthioalkyl, alkoxycarbonyl, alkylthiocarbonyl, amino, alkylamino, dialkylamino, aminosulfonyl, hydroxyl, perfluoroalkoxy, and alkylcarbonyl.

3. The compound or salt of claim 1, wherein $R^1$ is a 5 or 6-membered heterocyclyl group having at least one hetero atom selected from the group consisting of O, N, and S; a hydroxy $C_3$-$C_7$ cycloalkyl group; a N,N-di($C_1$-$C_6$ alkyl) amino $C_1$-$C_6$ alkyl group; a $C_1$-$C_6$ alkoxy $C_1$-$C_6$ alkyl group; N-benzyl piperadinyl; N-phenyl piperazinylalkyl; a phenyl $C_1$-$C_6$ alkyl group where the alkyl is substituted with a hydroxy group.

4. The compound or salt of claim 1, wherein $R^1$ is selected from the group consisting of the following:

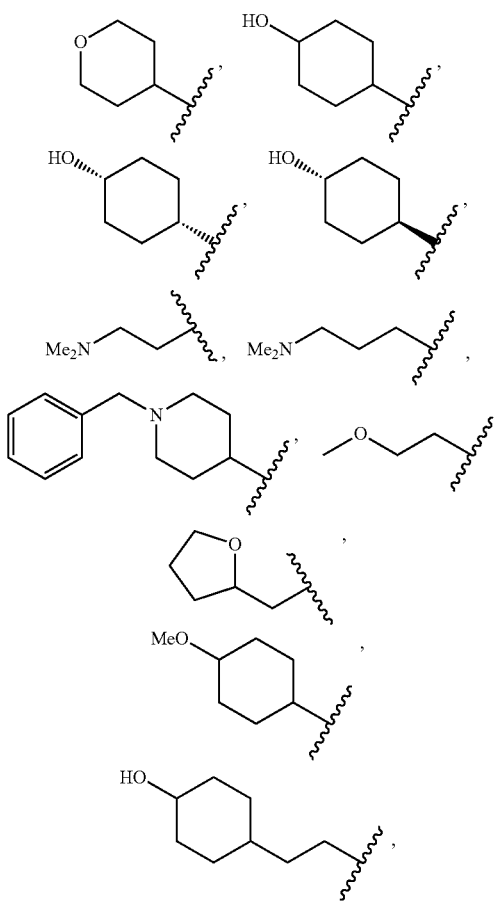

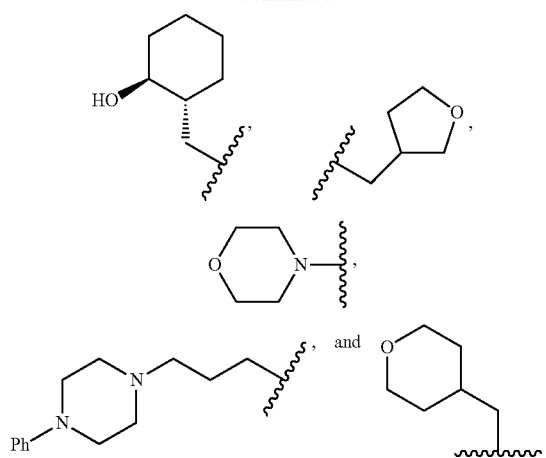

5. The compound or salt of claim 1, wherein $R^2$ is phenyl, $R^3$ is phenyl, $R^4$ is benzyl, and $R^1$ is selected from the group consisting of the following:

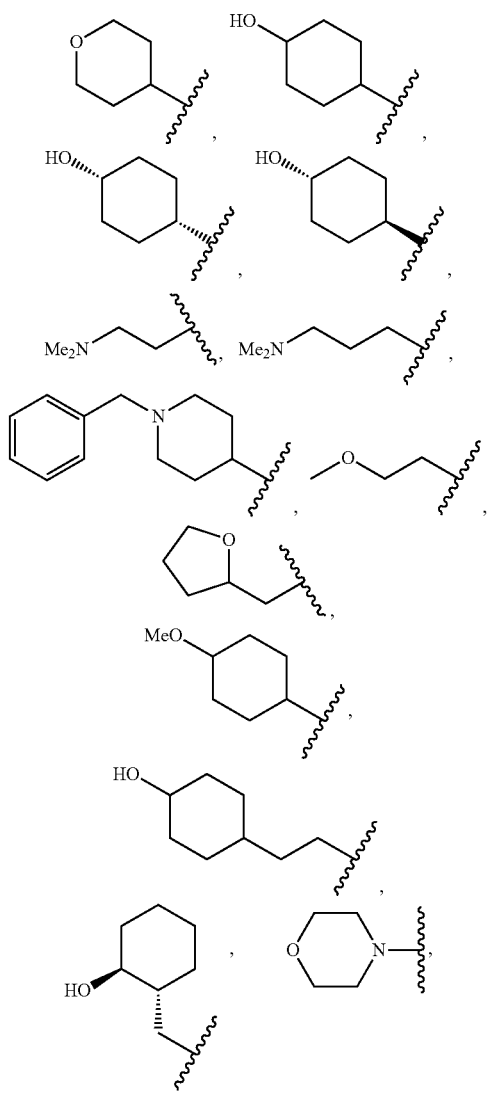

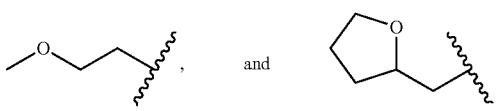

6. The compound or salt of claim 1, wherein $R^4$ is 4-methoxybenzyl, $R^2$ is phenyl, $R^3$ is phenyl, and $R^1$ is selected from the group consisting of the following:

7. The compound or salt of claim 1, wherein $R^4$ is phenylethyl, $R^2$ is phenyl, $R^3$ is phenyl, and $R^1$ is selected from the group consisting of the following:

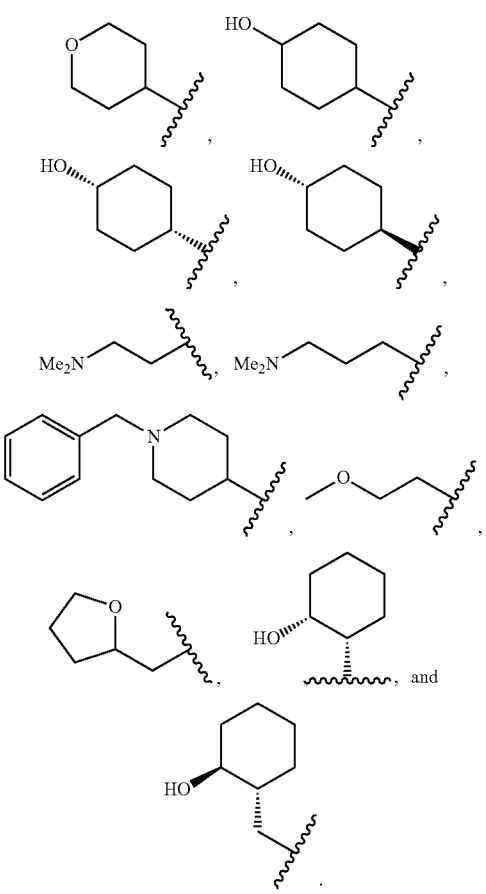

8. The compound or salt of claim 1, wherein $R^4$ is selected from 4-aminosulfonylbenzyl, 4-trifluoromethoxybenzyl, 4-methoxybenzyl, and cyclopropylmethyl and wherein $R^1$ is selected from the following:

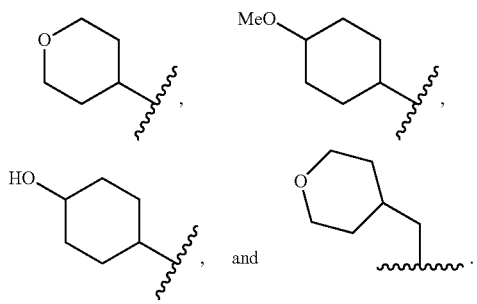

, and

9. A pharmaceutical composition comprising a compound or salt of claim 1 and a pharmaceutically acceptable carrier.

10. A compound of formula (I):

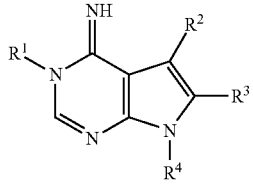

(I)

wherein $R^1$ is selected from the group consisting of alkyl, hydroxyalkyl, thioalkyl, alkoxyalkyl, alkylthioalkyl, cycloalkyl, hydroxycycloalkyl, hydroxycycloalkylalkyl, thiocycloalkyl, alkoxycycloalkyl, alkylthiocycloalkyl, dialkylaminoalkyl, heterocyclyl, heterocyclylalkyl, heteroaryl, arylalkyl, arylalkylpiperidin-4-yl, and arylpiperazinylalkyl, $R^2$ is phenyl, optionally substituted with one or more substituents selected from the group consisting of halo, alkyl, hydroxyalkyl, thioalkyl, alkoxy, alkylthioalkyl, alkoxycarbonyl, alkylthiocarbonyl, amino, alkylamino, dialkylamino, and alkylcarbonyl, $R^3$ is phenyl, optionally substituted with one or more substituents selected from the group consisting of halo, alkyl, hydroxyalkyl, thioalkyl, alkoxy, alkylthioalkyl, alkoxycarbonyl, alkylthiocarbonyl, amino, alkylamino, dialkylamino, and alkylcarbonyl, $R^4$ is benzyl, wherein the phenyl ring is substituted with one or more substituents selected from ethyl, propyl, isopropyl, n-butyl, sec-isobutyl, tert-butyl, pentyl, isoamyl, hexyl, hydroxyalkyl, thioalkyl, alkoxy, alkylthioalkyl, alkoxycarbonyl, alkylthiocarbonyl, amino, alkylamino, dialkylamino, aminosulfonyl, hydroxyl, perfluoroalkoxy, and alkylcarbonyl, or a pharmaceutically acceptable salt thereof, wherein $R^1$ is optionally substituted on the aryl and/or alkyl portion with one or more substituents selected from the group consisting of halo, alkyl, hydroxyalkyl, thioalkyl, alkoxy, alkylthioalkyl, alkoxycarbonyl, alkylthiocarbonyl, amino, alkylamino, dialkylamino, aminosulfonyl, hydroxyl, perfluoroalkoxy, alkylenedioxy, and alkylcarbonyl.

11. The compound or salt of claim 1, wherein $R^4$ is benzyl, wherein the phenyl ring is optionally substituted with one or more substituents selected from the group consisting of ethyl, propyl, isopropyl, n-butyl, sec-isobutyl, tert-butyl, pentyl, isoamyl, hexyl, hydroxyalkyl, thioalkyl, alkoxy, alkylthioalkyl, alkoxycarbonyl, alkylthiocarbonyl, amino, alkylamino, dialkylamino, aminosulfonyl, hydroxyl, perfluoroalkoxy, and alkylcarbonyl.

12. The compound or salt of claim 10, wherein $R^1$ is a 5 or 6-membered heterocyclyl group having at least one hetero atom selected from the group consisting of O, N, and S; a hydroxy $C_3$-$C_7$ cycloalkyl group; a hydroxy $C_1$-$C_6$ alkyl group; a N,N-di($C_1$-$C_6$ alkyl)amino $C_1$-$C_6$ alkyl group; a $C_1$-$C_6$ alkoxy $C_1$-$C_6$ alkyl group; a heterocyclyl $C_1$-$C_6$ alkyl group; phenyl $C_1$-$C_6$ alkyl group where the phenyl ring is substituted with one or more $C_1$-$C_6$ alkoxy groups; N-benzyl piperadinyl; N-phenyl piperazinylalkyl; or a phenyl $C_1$-$C_6$ alkyl group where the alkyl is substituted with a hydroxy group.

13. The compound or salt of claim 10, wherein $R^1$ is selected from the group consisting of the following:

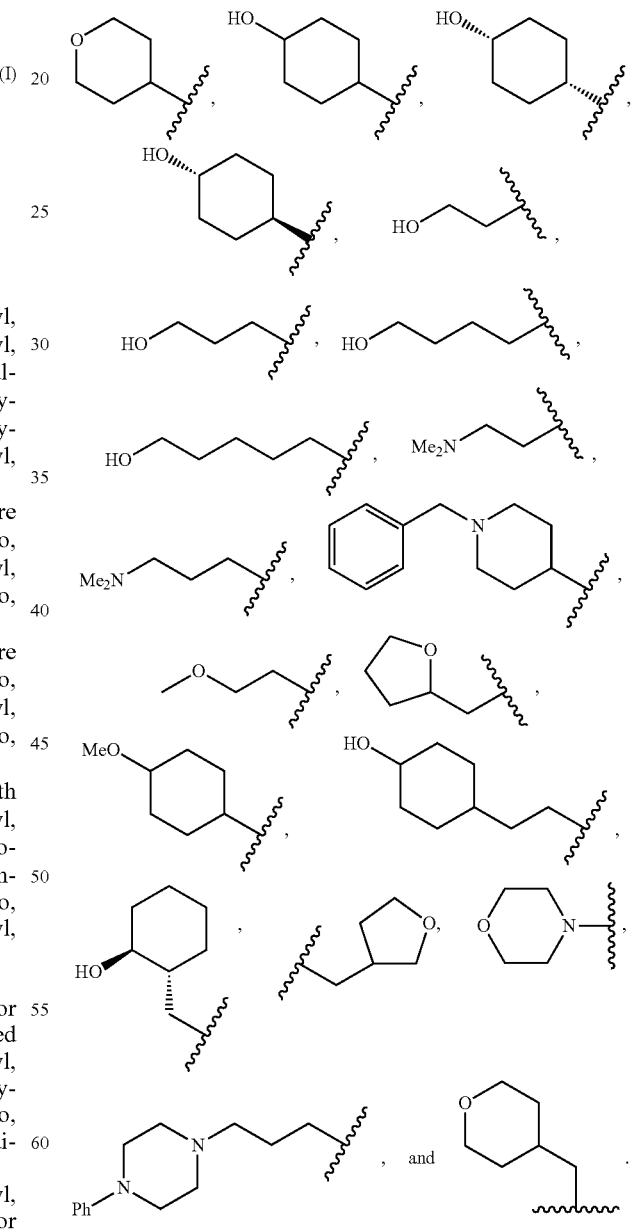

, and

14. The compound or salt of claim 10, wherein $R^2$ is phenyl, $R^3$ is phenyl, $R^4$ is substituted benzyl, and $R^1$ is selected from the group consisting of the following:

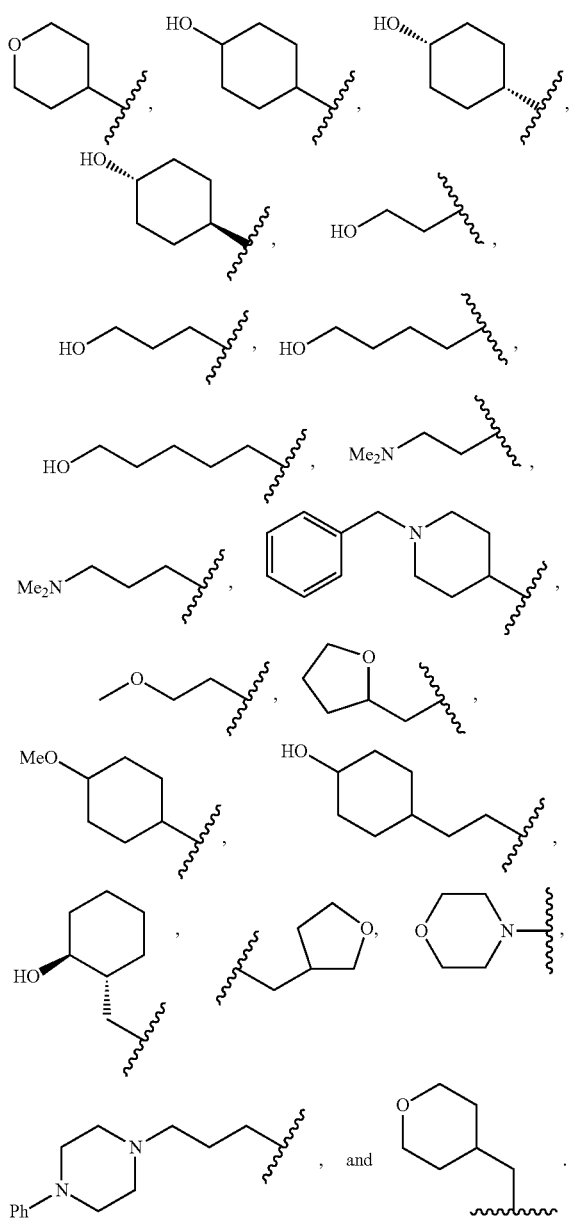

15. The compound or salt of claim 10, wherein R⁴ is 4-methoxybenzyl, R² is phenyl, R³ is phenyl, and R¹ is selected from the group consisting of the following:

16. The compound or salt of claim 10, wherein R⁴ is selected from 4-aminosulfonylbenzyl, 4-trifluoromethoxybenzyl, and 4-methoxybenzyl and wherein R¹ is selected from the following:

17. A pharmaceutical composition comprising a compound or salt of claim 10 and a pharmaceutically acceptable carrier.

18. The compound or salt of claim 5, wherein R² is phenyl, R³ is phenyl, R⁴ is benzyl, and R¹ is selected from the group consisting of the following:

19. The compound or salt of claim 18, wherein R² is phenyl, R³ is phenyl, R⁴ is benzyl, and R¹ is:

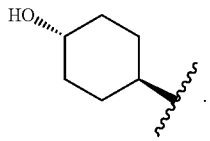 [SMILES: *[C@H]1CC[C@H](O)CC1]

* * * * *

UNITED STATES PATENT AND TRADEMARK OFFICE
CERTIFICATE OF CORRECTION

PATENT NO.         : 9,663,521 B2                                Page 1 of 1
APPLICATION NO.    : 14/364759
DATED              : May 30, 2017
INVENTOR(S)        : Frankowski et al.

It is certified that error appears in the above-identified patent and that said Letters Patent is hereby corrected as shown below:

On the Title Page

Item (72), Replace the listed inventors with the following:
Kevin Frankowski, Lawrence, KS (US); Samarjit Patnaik, Gaithersburg, MD (US); Sui Huang, Chicago, IL (US); Juan Jose Marugan, Gaithersburg, MD (US); John Norton, San Diego, CA (US); Frank J. Schoenen, Lawrence, KS (US); Noel Terrence Southall, Potomac, MD (US); Steven Titus, Elkridge, MD (US); Wei Zheng, Potomac, MD (US); Chen Wang, Chicago, IL (US).

Signed and Sealed this
Twentieth Day of November, 2018

Andrei Iancu
*Director of the United States Patent and Trademark Office*